US006942852B1

(12) United States Patent
Offord et al.

(10) Patent No.: US 6,942,852 B1
(45) Date of Patent: Sep. 13, 2005

(54) N-TERMINAL MODIFICATIONS OF RANTES AND METHODS OF USE

(75) Inventors: Robin E. Offord, Bernex (CH); Darren Thompson, Santa Cruz, CA (US); Jill Wilken, San Francisco, CA (US)

(73) Assignee: Gryphon Therapeutics, Inc., South San Francisco, CA (US)

( * ) Notice: Subject to any disclaimer, the term of this patent is extended or adjusted under 35 U.S.C. 154(b) by 504 days.

(21) Appl. No.: 09/678,851

(22) Filed: Oct. 4, 2000

Related U.S. Application Data

(63) Continuation of application No. 08/141,833, filed on Aug. 28, 1998, now Pat. No. 6,168,784.
(60) Provisional application No. 60/056,292, filed on Sep. 3, 1997, provisional application No. 60/077,874, filed on Mar. 13, 1998, and provisional application No. 60/090,834, filed on Jun. 26, 1998.

(51) Int. Cl.$^7$ .......................... A61K 38/19; C07K 14/52

(52) U.S. Cl. ........................... 424/85.1; 514/2; 514/12; 530/300; 530/324

(58) Field of Search .................. 424/85.1; 514/2, 514/12; 530/300, 324; 536/300, 324

(56) References Cited

U.S. PATENT DOCUMENTS

| 5,122,614 A | 6/1992 | Zalipsky ...................... 548/520 |
| 5,672,662 A | 9/1997 | Harris et al. ................. 525/408 |
| 5,739,208 A | 4/1998 | Harris ......................... 525/54.1 |
| 6,168,784 B1 * | 1/2001 | Offord et al. ............... 424/85.1 |

FOREIGN PATENT DOCUMENTS

| EP | 0 605 963 A2 | 12/1993 |
| WO | 96/17935 | 6/1996 |
| WO | 96/34878 | 11/1996 |

OTHER PUBLICATIONS

Rudinger, Peptide Hormones (Ed. J. Parsons, Jun. 1976) pp. 1–6.*
Abuchowski, Abraham, et al., "Alteration of Immunological Properties of Bovine Serum Albumin by Covalent Attachment of Polyethylene Glycol", *J. Biol. Chem.*, vol. 252, No. 11, pp. 3578–3581 (1977).
Alkhatib, Ghalib, et al., "CC CKR5: A RANTES, MIP–1α, MIP–1β Receptor as a Fusion Cofactor for Macrophage–Tropic HIV–1", *Science*, vol. 272, pp. 1955–1958 (1996).
Angiolillo, et al., "A Role for the Interferon–Inducible Protein 10 in Inhibition of Angiogenesis by Interleukin–12", *Annals NY Acad. Sci.*, vol. 795, pp. 158–167 (1996).
Arenzana–Seisdedos, Fernando, et al., "HIV Blocked by Chemokine Antagonist", *Nature*, vol. 383, p. 400 (1996).
Berger, et al., "A New Classification for HIV–1", *Nature*, vol. 391, p. 240 (1998).

Cairns, et al., "Chemokines and HIV–1 Second Receptors: The Therapeutic Connection", *Nature Med.*, vol. 4, No. 5, pp. 563–568 (1998).
Chen, et al., "Genetically Divergent Strains of Simian Immunodeficiency Virus Use CCR5 as a Co–Receptor for Entry", *J. Virol.*, vol. 71, No. 4, pp. 2705–2714 (1997).
Chesebro, et al., "Mapping of Independent V3 Envelope Determinants of Human Immunodeficiency Virus Type 1 Macrophage Tropism and Syncytium Formation in Lymphocytes", *J. Virol.*, vol. 70, No. 12, pp. 9055–9059 (1996).
Choe, et al., "The β–Chemokine Receptors CCR3 and CCR5 Facilitate Infection by Primary HIV–1 Isolates", *Cell* vol. 85, pp. 1135–1148 (1996).
Cocchi, et al., "Identification of RANTES, MIP–1α, and MIP–β as the the Major HIV–Suppressive Factors Produced by CD8+ T Cells", *Science*, vol. 270, pp. 1811–1815 (1995).
Cocchi, et al., "The V3 Domain of the HIV–1 gp 120 Envelope Glycoprotein is Critical for Chemokine–Mediated Blockade of Infection", *Nature Med.*, vol. 2, No. 11, pp. 1244–1247 (1996).
Connor, et al., "Increased Viral Burden and Cytopathicity Correlate Temporally with CD4+ T–Lymphocyte Decline and Clinical Progression in Human Immunodeficiency Virus Type 1–Infected Individuals", *J. Virol.*, vol. 67, No. 4, pp. 1772–1777 (1993).
Danesi, et al., "Inhibition of Experimental Angiogenesis by the Somatostatin Analogue Octretide Acetate (SMS 201–995)$^1$", *Clin. Cancer Res.*, vol. 3, pp. 265–272 (1997).
Datema., et al., "Antiviral Efficacy in Vivo of the Anti–Human Immunodeficiency Virus Bicyclam SDZ SID 791 (Jm3100), an Inhibitor of Infectious Cell Entry", *Antimicrob. Agents and Chemo.*, vol. 40, No3., pp. 750–754 (1996).
Dawson, et al., "Synthesis of Proteins by Native Chemical Ligation", *Science*, vol. 266, pp. 776–779 (1994).
Deng, et al., "Identification of a Major Co–Receptor for Primary Isolates of HIV–1", *Nature*, vol. 381, pp. 661–666 (1996).
Doranz, et al., "A Dual–Tropic Primary HIV–1 Isolate That Uses Fusin and the β–Chemokine Receptors CKR–5, CKR–3, and CKR–2B as Fusion Cofactors", *Cell*, vol. 85, pp. 1149–1158 (1996).
Friedlander, et al. "Definition of Two Angiogenic Pathways by Distinct α, Integrins", *Science*, vol. 270, pp. 1500–1502 (1995).

(Continued)

*Primary Examiner*—Bennett Celsa
(74) *Attorney, Agent, or Firm*—Liniak, Berenato & White; Catherine Joyce; Jeffrey Auerbach

(57) ABSTRACT

N-terminally modified RANTES derivatives are disclosed. The derivatives effectively block the inflammatory effects of RANTES, and are useful for the treatment of asthma, allergic rhinitis, atopic dermatitis, atheroma/atherosclerosis, and rheumatoid arthritis. Additionally, the compounds are useful for the treatment of HIV infection.

22 Claims, 8 Drawing Sheets

OTHER PUBLICATIONS

Gao, et al., "Structure and Functional Expression of the Human Macrophage Inflammatory Protein 1α/RANTES Receptor", *J. Exp. Med.*, vol. 177, pp. 1421–1427 (1993).

Gauduin, et al., "Passive Immunization with a Human Monoclonal Antibody Protects hu–PBL–SCID Mice Against Challenge by Primary Isolate of HIV–1", *Nat. Med.*, vol. 3, No. 12, pp. 1389–1393 (1997).

Hojo, Hironobu and Aimoto, Saburo, "Polypeptide Synthesis Using the S–Alkyl Thioester of a Partially Protected Peptide Segment. Synthesis of the DNA–Binding Domain of c–Myb Protein (142–193)–NH$_2$", *Bull.Chem.Soc.Jpn.*, vol. 64, pp. 111–117 (1991).

Jose, et al., "Eotaxin: A Potent Eosinophil Chemoattractant Cytokine Detected in a Guinea Pig Model of Allegric Airways Inflammation", *J.Exp.Med.*, vol. 179, pp. 881–887 (1994).

Mack, et al., "Aminooxypentane–RANTES Induces CCR5 Internalization but Inhibits Recycling: A Novel Inhibitory Mechanism of HIV Infectivity", *J.Exp.Med.*, vol. 187, No. 8, pp. 1215–1224 (1998).

Mosier, et al., "Transfer of a Functional Human Immune System to Mice With Severe Combined Immunodeficiency", *Nature*, vol. 335, pp. 256–259 (1988).

Mosier, et al., "Human Immunodeficiency Virus Infection of Human–PBL–SCID Mice", *Science*, vol. 251, pp. 791–794 (1991).

Mosier, et al, "Rapid Loss of CD4+ T Cells in Human–PBL–SCID Mice by Noncytopathic HIV Isolates", *Science*, vol. 260, pp. 689–692 (1993).

Mosier, Donald, "Human Immunodeficiency Virus Infection of Human Cells Transplanted to Severe Combined Immunodeficient Mice", *Adv.in Immun.*, vol. 63, pp. 79–125 (1996).

McKnight, et al., "HIV–2 and SIV Infection of Nonprimate Cell Lines Expressing Human CD4: Restrictions to Replication at Distinct Stages", *Virology*, vol. 201, pp. 8–18 (1994).

Neote, et al., "Molecular Cloning, Functional Expression, and Signaling Characteristics of a C–C Chemokine Receptor", *Cell*, vol. 72, pp. 415–425 (1993).

Oikawa, et al., "Angiogenic Factor of a rat Mammary Tumor Cell Line (RMT–1) (I). Secretion of two Distinct Angiogenic Factors Into Serum–Free Conditioned Medium by RMT–1 Cells", *Cancer Lett.*, vol. 59, pp. 57–66 (1991).

Parren, et al., "Protection Against HIV–1 Infection in hu–PBL–SCID Mice by Passive Immunization With a Neutralizing Human Monoclonal Antibody Against the gp120 CD4 Binding Site", *AIDS*, vol. 9, No. 6, pp. 1–6 (1995).

Paxton, et al., "Reduced HIV–1 Infectability of CD4+ Lymphocytes From Exposed–Unifected Individuals: Association With Low Expression of CCR5 And High Production of β–Chemokines", *Virology*, vol. 244, pp. 66–73 (1998).

Picchio, et al., "Chemokine Receptor CCR5 Genotype Influnces the Kinetics of Human Immunodeficiency Virus Type 1 Infection in Human PBL–SCID Mice", *J. Virol.*, vol. 71, No. 9, pp 7124–7127 (1997).

Picchio, et al., "The Cell Tropism of Human Immunodeficiency Virus Type 1 Determines the Kinetics of Plasma Viremia in SCID Mice Reconstituted With Human Peripheral Blood Leukocytes", *J.Virol.*, vol. 72, No. 3, pp. 2002–2009 (1998).

Proudfoot, et al., "Extension of Recombinant Human RANTES by the Retention of the Initiating Methionine Produces a Potent Antagonist", *J.Biol.Chem.*, vol. 271, No. 5, pp. 2599–2603 (1996).

Risau, Werner, "Mechanisms of Angiogenesis", *Nature*,vol. 386, pp. 671–674 (1997).

Schnolzer, et al., "In situ neutralization in Boc–chemistry Solid Phase Peptide Synthesis", *J.Peptide Protein Res.*, vol. 40, pp. 180–193 (1992).

Schuitemaker, et al., "Monocytotropic Human Immunodeficiency Virus Type 1 (HIV–1) Variants Detectable in all Stages of HIV–1 Infection Lack T–Cell Line Tropism and Syncytium–Inducing Ability in Primary T–Cell Culture", *J. Virol.*, vol.. 65, No. 1, pp. 356–363 (1991).

Simmons, et al., "Potent Inhibition of HIV–1 Infectivity in Macrophages and Lymphocytes by a Novel CCR5 Antagonist", *Science*, vol. 276, pp. 276–279 (1997).

Simmons, et al., "Primary, Syncytium–Inducing Human Immunodeficiency Virus Type 1 Isolates Are Dual–Tropic and Most Can Use Either Lestr or CCR5 as Coreceptors for Virus Entry", *J.Virol.*, vol. 70, No. 12, pp. 8355–8360 (1996).

Speck, et al., "Selective Employment of Chemokine Receptors as Human Immunodeficiency Virus Type 1 Coreceptors Determined by Individual Amino Acids within the Envelope V3 Loop", *J.Virol.*, vol. 71, No. 9, pp. 7136–7139 (1997).

Tersmette, et al., "Association Between Biological Properties of Human Immunodeficiency Virus Variants and Risk for Aids and Aids Mortality", *Lancet*, pp. 983–985 (1989).

Trkola, et al., "CD4–Dependent, Antibody–Sensitive Interactions Between HIV–1 and its Coreceptor CCR–5", *Nature*, vol. 384, pp. 184–187 (1996).

Trkola, et al., "Genetic Subtype–Independent Inhibition of Human Immunodeficiency Virus Type 1 Replication by CC and CXC Chemokines", *J. Virol.*, vol. 72, No. 1, pp. 396–404 (1998).

Tsutsumi, et al., "Chemical Modification of Natural Human Tumor Necrosis Factor–α With Polyethylene Glycol Increases its Anti–Tumor Potency", *Jpn.J. Cancer Res.*, vol. 85, pp. 9–12 (1994).

Weiss, et al., "Plasma Levels of Monocyte Chemoattractant Protein–1 but not Those of Macrophage Inhibitory Protein–1α and RANTES Correlate with Virus Load in Human Immunodeficiency Virus Infection", *J.Infect.Dis.*, vol. 176, No. 6, pp. 1621–1624 (1997).

Wu, et al., "CCR5 Levels and Expression Pattern Correlate with Infectability by Macrophage–Tropic HIV–1 In Vitro", *J.Exp.Med.*, vol. 185, No. 9, pp. 1681–1691 (1997).

Zalipsky, Samuel, "Functionalized Poly(ethylene glycol) for Preparation of Biologically Relevant Conjugates", *Bioconj. Chem.*, vol. 6, pp. 150–165 (1995).

International Search Report for PCT/US98/18204.

\* cited by examiner

| cons | C T R P N H N T R K - - S I H I G P G R A F Y T T G E I I G D I R Q A H C |
|---|---|
| 242   | - - - - - - - - - - - - - - - - - - - - - - - - - - - - - - - - - - - |
| 242/H | - - - - - - - - R X X - S - - - - - - - - - - R - X - - - - - - - - - |
| 241   | - - - - - - - - R X X - S - - - - - - - - - - H - X - Q - - - - - - - |
| 230   | - - - - - - - - R X X - S - - - - - - - - - - R - X - Q - V - M L - - |
|       |   |
| mous  |   |
| 1     | - - - - - - - - R X X - S - - - - - - - - - - H - X - - - - - - - - - |
| 2     | - - - - - - - - R X X - S - - - - - - - - - - H - X - - - - - - - - - |
| 3     | - - - - - - - - R X X - S - - - - - - - - - - R - X - - - - - - - - - |
| 4     | - - - - - - - - R X X - S - - - - - - - - - - H - X - - - - - - - - - |

FIGURE 3

N-TERMINAL MODIFICATIONS OF RANTES AND METHODS OF USE

CROSS-REFERENCE TO RELATED APPLICATIONS

This application is a continuation of U.S. patent application Ser. No. 08/141,833, filed on Aug. 28, 1998 (now U.S. Pat. No. 6,168,784) which application claims priority from Provisional Application No. 60/056,292 (filed Sep. 3, 1997), Provisional Application No. 60/077,874 (filed Mar. 13, 1998), and Provisional Application No. 60/090,834 (filed Jun. 26, 1998), all of which applications are hereby incorporated by reference herein in their entirety.

TECHNICAL FIELD

The invention relates to N-terminally modified RANTES derivatives that effectively block the inflammatory effects of RANTES, and are thus useful for the treatment of asthma, allergic rhinitis, atopic dermatitis, atheroma/atheroschleosis, and rheumatoid arthritis. Additionally, the compounds are useful for the treatment of human immune deficiency virus ("HIV").

BACKGROUND

The protein known as RANTES is a member of a large family of cytokines known as chemokines, and is classified as a β-chemokine. It has a sixty-eight amino acid sequence (SEQ ID NO:1). A receptor for RANTES has recently been cloned (Gao, et al., *J. Exp. Med.* 177:1421–7 (1993); Neote, et al., *Cell* 72:415–25 (1993)), which has been shown to bind chemokines in the order of potency of MIP-1α>RANTES.

Chemokines have the ability to recruit and activate a wide variety of proinflammatory cell types, and RANTES has been shown to elicit an inflammatory response in vivo. RANTES, along with the natural ligands for the CCR5 chemokine receptor, MIP-1α, MIP-1β, were found to inhibit human immune deficiency virus type-1 ("HIV-1") infection (Cocchi, et al., *Science* 270:1811–1815 (1995)), leading to the identification of CCR5 as the major co-receptor for primary isolates of HIV-1, HIV-2 and SIV-1 (Deng, et al., *Nature* 381:661–666 (1996); Doranz, et al., *Cell* 85:1149–1158 (1996); Choe, et al., *Cell* 85:1135–1148 (1996); Chen, et al., *J. Virol.* 71:2705–2714 (1997); and Alkhatib, et al., *Science* 272:1955–1958 (1996)). However, although RANTES consistently inhibits HIV-1 replication in peripheral blood mononuclear cells, it does not block infection of primary macrophage cultures, which suggests that RANTES would not influence HIV replication in non-lymphocyte cell types.

N-terminal modifications of RANTES result in antagonists that can block HIV-1 infection without signaling calcium flux (Mack, et al., *J. Exp. Med.* 187:1215–1224 (1998) and Proudfoot, et al., *J. Biol. Chem.* 271:2599–2603 (1996)). These modifications include N-terminal truncation [RANTES 9-68] (Arenzana-Seisdedos, et al., *Nature* 383:400 (1996)), and addition of methionine ("Met-RANTES") or aminooxypentane ("AOP-RANTES") at the N-terminus of RANTES (Mack, et al., supra and Simmons, et al., *Science* 276:276–279 (1997)). It has been reported that the Met-RANTES and AOP-RANTES derivatives are antagonists of RANTES. Further, N-terminally modified RANTES, with a higher affinity for CCR5 than native RANTES are more potent than native RANTES in blocking infection (Simmons, et al., supra).

Chemokine receptor antagonists that are potent, selective, and achieve full receptor occupancy would clearly be useful for the treatment of HIV-1 in infected individuals. Surprisingly, compounds have been discovered with this spectrum of activity. These derivatives inhibited infection of many different cell types, including macrophages and lymphocytes.

Additionally, antagonists of RANTES effectively block its inflammatory effects, and are thus usefll for the treatment of asthma, allergic rhinitis, atopic dermatitis, viral diseases, atheroma/atheroschleosis, rheumatoid arthritis and organ transplant rejection.

Certain derivatives of RANTES are disclosed in Wells, et al., International Application WO 96/17935.

SUMMARY OF THE INVENTION

The polypeptides provided by the present invention are derivatives of RANTES modified at the N-terminus; they are antagonists of RANTES, and/or of MIP-1α, and/or MIP-1β.

The polypeptides have the general formula:

$$R^1\text{-RANTES (2-68) (SEQ ID NO:2)}$$

where $R^1$ is $CH_3$—$(CH_2)_n$—X—; in which X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond; and n is an integer from 4–8.

Also provided are pharmaceutical compositions and methods of treating disease states, including HIV infection, by administering therapeutically effective amounts of compounds comprising RANTES derivatives, or pharmaceutically acceptable salts thereof.

The invention also provides for polypeptides of the formula $R^1$-RANTES (2-68) (SEQ ID NO:2) that have been modified by the grafting of polyethylene glycol ("PEG") chains or PEG-based chains onto the RANTES portion of the polypeptide.

BRIEF DESCRIPTION OF THE DRAWINGS

FIG. 3 depicts the partial sequences of several HIV-1 clones:cons (SEQ ID NO:7), 242 (SEQ ID NO:8), 242/H (SEQ ID NO:9), 241 (SEQ ID NO:10), 230 (SEQ ID NO:11) and mouse 1–4 (SEQ ID NO:9).

FIG. 7A shows infection with the R5 SF162 isolate and FIG. 7B shows infection with two R5 variants of HIV-I 242.

DESCRIPTION OF SPECIFIC EMBODIMENTS

Figure 1:
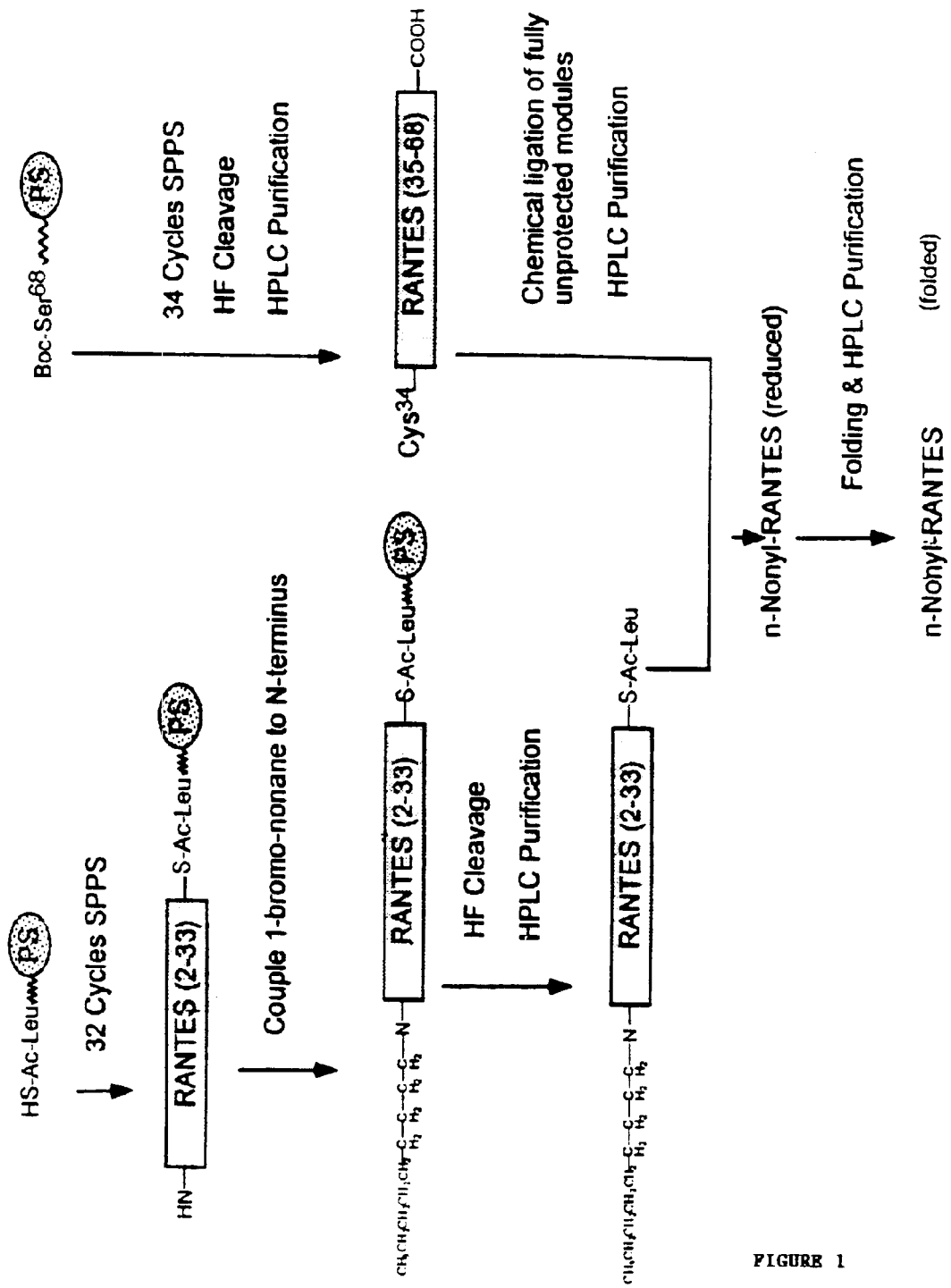
FIG. 1 illustrates the chemical synthesis of n-nonyl-RANTES (2-68) from HN-RANTES (2-33) (SEQ ID NO:3) and Cys$^{34}$-RANTES (35-68) (SEQ ID NO:4).

RANTES (SEQ ID NO:1) has the sequence:

SPYSSDT TPCCFAYIAR PLPRAHIKEY FYTSGKCSNP
AVVFVTRKNR QVCANPEKKW VREYINSLEM S

The polypeptides of the present invention thus have the sequence: (SEQ ID NO:2)

$R^1$—X-PYSSDT TPCCFAYIAR PLPRAHIKEY FYTSGKCSNP
AVVFVTRKNR QVCANPEKKW VREYINSLEM S or have a sequence which is substantially homologous with any of the above sequences. Stated another way, the polypeptides of the invention have the general formula:

$R^1$-RANTES (2-68) (SEQ ID NO:2)

where $R^1$ is $CH_3$—$(CH_2)_n$—X—; in which X is —C(O)—NH—$CH_2$—C(O)—, —NHCH$_2$—C(O)—, —ONH—$CH_2$—C(O)—, —OCH$_2$—$CH_2$—(O)—, —CH=CH—C(O)—, —C(O)—, or a covalent bond; and n is an integer of 4–8; or a pharmaceutically acceptable salt thereof.

The term "substantially homologous" when used herein includes amino acid sequences having at least 40%, 50%, 60%, 70%, 80%, 90%, 95% or 99% sequence homology with the given sequence (99% preference). This term can include, but is not limited to, amino acid sequences having from 1 to 20, from 1 to 10 or from 1 to 5 single amino acid deletions, insertions or substitutions relative to a given sequence provided that the resultant polypeptide acts as an antagonist to RANTES.

It should be noted that it is well known in the art that certain amino acids can be replaced with others resulting in no substantial change in the properties of a polypeptide, including but not limited to conservative substitutions of amino acids. Such possibilities are within the scope of the present invention. It should also be noted that deletions or insertions of amino acids can often be made which do not substantially change the properties of a polypeptide. The present invention includes such deletions or insertions (which may be, for example up to 10, 20 or 50% of the length of the specific antagonists sequence given above).

The term "pharmaceutically acceptable salt" is used herein to mean a salt that retains the biological effectiveness and properties of the polypeptides of the invention and which are not biologically or otherwise undesirable. Salts may be derived from acids or bases. Acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like. Base addition salts may be derived from inorganic bases, and include sodium, potassium, lithium, ammonium, calcium, magnesium salts, and the like. Salts derived from organic bases include those formed from primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

It is well recognized that the properties of peptides can be enhanced by grafting organic chain-like molecules onto them. These molecules are often polyethylene glycol-based ("PEG"-based, i.e. based on the repeating unit —$CH_2CH_2O$—). See for example, Tsutsumi, et al, *Jpn. J. Cancer Res.* 85:9–12 (1994). PEG-based chains are amphiphilic, non-immunogenic and not susceptible to cleavage by proteolytic enzymes. Preparations of materials that have been modified by PEG or PEG-based chains, have reduced immunogenicity and antigenicity. See for example, Abuchowski, et al, *Journal of Biological Chemistry* 252(11): 3578–3581 (1977). PEG also serves to increase the molecular size of the material to which it is attached, thereby increasing its biological half-life. These beneficial properties of the PEG-modified materials make them very useful in a variety of therapeutic applications.

Accordingly this invention also contemplates improving the pharmacokinetics of $R^1$-RANTES (2-68) (SEQ ID NO:2). This can be achieved by the modification or "PEGylation" of the polypeptides of the invention, $R^1$-RANTES (2–68) (SEQ ID NO:2), at sites that are likely to permit the proteins to retain their intrinsic biological activity. Such sites include, but not limited to, the C-terminus of the polypeptide. The grafting of PEG chains or PEG-based chains onto proteins is known. See for example, Zalipsky, U.S. Pat. No. 5,122,614, which describes PEG that is converted into its N-succinimide carbonate derivative. Also known are PEG chains modified with reactive groups to facilitate grafting onto proteins. See for example, Harris, U.S. Pat. No. 5,739,208, which describes a PEG derivative that is activated with a sulfone moiety for selective attachment to thiol moieties on molecules and surfaces and Harris, et al., U.S. Pat. No. 5,672,662, which discloses active esters of PEG acids that have a single propionic or butanoic acid moiety. This area is extensively reviewed in Zalipsky, *Bioconjugate Chemistry* 6:150–165 (1995). Besides use of PEG, Wright, EP 0 605 963 A2 describes linking reagents that contain water soluble polymers that form a hydrazone linkage with an aldehyde group on a protein. All of the aforementioned references are incorporated herein by reference.

As noted above, the polypeptides of the invention have the general formula $R^1$-RANTES (2-68), (SEQ ID NO:2) where $R^1$ is $CH_3$—$(CH_2)_n$—X—; in which X is selected from the group consisting of —C(O)—NH—$CH_2$—C(O)—, —NHCH$_2$—C(O)—, —ONH—$CH_2$C(O)—, —OCH$_2$—$CH_2$—C(O)—, —CH=CH—C(O)—, —C(O)—, and a covalent bond; and n is an integer from 4–8. Polypeptides of particular interest include those listed below:

| Name | n | X |
| --- | --- | --- |
| n-hexanoyl-[Gly$^1$]RANTES (2-68) (SEQ ID NO:5) | 4 | —C(O)—NH—CH$_2$—C(O)— |
| n-nonanoyl-RANTES (2-68)$^a$ (SEQ ID NO:2) | 7 | —C(O)— |
| n-hexyl-[Gly$^1$]RANTES (2-68) (SEQ ID NO:5) | 5 | —NHCH$_2$—C(O)— |
| n-nonyl-RANTES (2-68) (SEQ ID NO:2) | 8 | covalent bond |

-continued

| Name | n | X |
|---|---|---|
| n-pentyloxy-[Gly¹]RANTES (2-68) (SEQ ID NO:5) | 4 | —ONH—CH$_2$—C(O)— |
| 3-pentyloxypropan-1-oyl-RANTES (2-68) (SEQ ID NO:2) | 4 | —OCH$_2$—CH$_2$—C(O)— |
| non-2-en-1-ylRANTES (2-68) (SEQ ID NO:2) | 5 | —CH=CH—C(O)— |

[a]n-nonanoyl-RANTES (2-68) is sometime referred to herein as NNY-RANTES

The polypeptides of the present invention are useful for blocking the effects of RANTES and/or MIP-1α in mammals with respect to the recruitment and/or activation of pro-inflammatory cells. The present invention is therefore useful as an anti-inflammatory agent in the treatment of diseases such as asthma, allergic rhinitis, atopic dermatitis, atheroma/atherosclerosis and rheumatoid arthritis.

M-tropic HV viruses, also referred to as "R5" viruses, enter cells via the CD4 and CCR5 receptors. T-tropic viruses, also referred to as "X4" viruses, enter cells via the CD4 and CXCR4 receptors. Dual-tropic viruses, also referred to as "R5×4" viruses, mediate entry via more than one of the co-receptors. For example, HIV-1 242 is an M-tropic or R5 virus. HIV-1 230 is a T-tropic or X4 virus. HIV-1 241 is a dual-tropic or R5X4 virus. Chesebro, et al., *J. Virol.* 70:9055–9059 (1996); Speck, et al., *J. Virol.* 71:7136–7139 (1997). For nomenclature classifications of HIV-1 isolates by co-receptor, see Berger, et al., *Nature* 391: 240 (1998).

A preferred use of the polypeptides of the present invention is in inhibiting HIV-1 infection in mammals.

The used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

The term "a disease state in mammals that is alleviated by treatment with a RANTES inhibitor" as used herein is intended to cover all disease states which are generally acknowledged in the art to be usefully treated with RANTES inhibitors in general, and those disease states which have been found to be usefully treated by the specific compounds of our invention. These include, by way of illustration and not limitation, asthma, allergic rhinitis, atopic dermatitis, viral diseases, atheroma/atheroschleosis, rheumatoid arthritis and organ transplant rejection.

As used herein, the term "therapeutically effective amount" refers to that amount of a polypeptide of the invention which, when administered to a mammal in need thereof, is sufficient to effect treatment (as defined above), for example, as an anti-inflammatory agent, anti-asthmatic agent, an immunosuppressive agent, or anti-autoimmune disease agent to inhibit HIV-1 infection in mammals. The amount that constitutes a "therapeutically effective amount" will vary depending on the polypeptide, the condition or disease and its severity, and the mammal to be treated, its weight, age, etc., but may be determined routinely by one of ordinary skill in the art with regard to contemporary knowledge and to this disclosure.

As used herein, the term "q.s." means adding a quantity sufficient to achieve a stated function, e.g., to bring a solution to a desired volume (e.g., 100 mL).

Methods of Preparation

The polypeptides of the present invention are prepared by a combination of chemical synthesis and chemical ligation techniques.

The synthesis of proteins by native chemical ligation is disclosed in International Patent Application PCT/US95/05668, International Publication Number WO 96/34878, and a method of preparing proteins chemically modified at the N-terminal is disclosed in provisional Patent Application 06/050,420, filed May 29, 1997, the disclosures of which are incorporated herein by reference. In general, a first oligopeptide containing a C-terminal thioester is reacted with a second oligopeptide with an N-terminal cysteine having an unoxidized sulfhydryl side chain. The unoxidized sulfhydryl side chain of the N-terminal cysteine is condensed with the C-terminal thioester in the presence of a catalytic amount of a thiol, preferably benzyl mercaptan, thiophenol, 2-nitrothiophenol, 2-thiobenzoic acid, 2-thiopyridine, and the like. An intermediate oligopeptide is produced by linking the first and second oligopeptides via a β-aminothioester bond, which rearranges to produce an oligopeptide product comprising the first and second oligopeptides linked by an amide bond.

REACTION SCHEME I

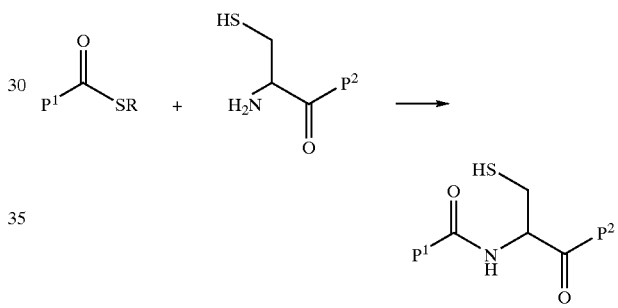

where P¹ is the first oligopeptide attached to a C-terminal thioester; R is, for example benzyl; and P² is the second oligopeptide attached to an N-terminal cysteine having an unoxidized sulfhydryl side chain.

The polypeptides of the present invention are prepared as follows. The first oligopeptide having a C-terminal thioester comprises the RANTES amino acid sequence 2-33 (SEQ ID NO:3) at the 1-position, and is identified as formula (4) below. This is prepared by solid phase peptide synthesis on a thioester producing resin to give the compound of formula (2). The N-terminus of this material is then chemically modified, for example by direct coupling of n-hexanoic acid to the resin to yield a compound of formula (3), followed by cleaving the product with hydrogen fluoride to yield the compound of formula (4). The chemically modified oligopeptide (4) is then purified, preferably by reverse-phase preparative HPLC.

REACTION SCHEME II

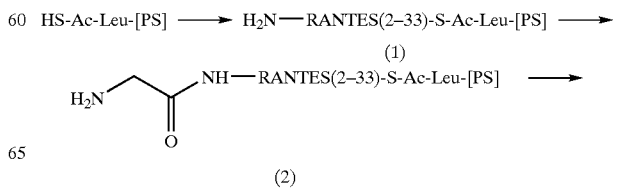

-continued

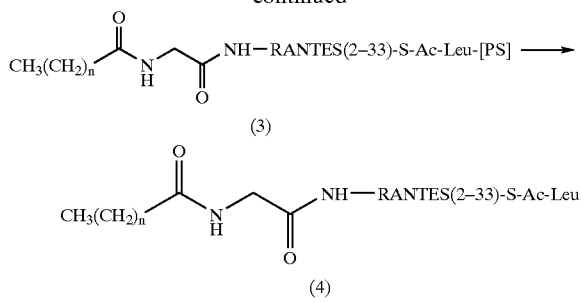

where PS is polymer support.

The second oligopeptide with an N-terminal cysteine having an unoxidized sulfhydryl side chain comprises the RANTES amino acid sequence 34–68 (SEQ ID NO:4), and is identified as formula (5) below. It is prepared by solid phase peptide synthesis on a Boc-Ser-OCH$_2$-Pam-resin, and is then cleaved with hydrogen fluoride. The oligopeptide with an N-terminal cysteine is then purified, preferably by reverse-phase preparative HPLC.

Reaction Scheme III

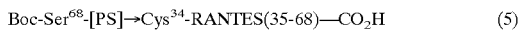

Boc-Ser$^{68}$-[PS]→Cys$^{34}$-RANTES(35-68)—CO$_2$H   (5)

The first oligopeptide of formula (4) is then chemically ligated with the second oligopeptide of formula (5) by the method disclosed above, to produce RANTES chemically modified at the N-terminal, which is folded and purified conventionally. Such polypeptides, would have the formula:

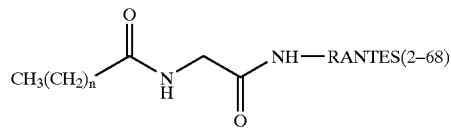

where X is —C(O)—NH—CH$_2$—C(O)—. Similarly, polypeptides of the invention having other "X" groups such as —NHCH$_2$—C(O)—, —ONH—CH$_2$C(O)—, —OCH$_2$—CH$_2$—C(O)—, —CH=CH—C(O)—, —C(O)—, or a covalent bond, can be synthesized in a similar manner by using different materials to modify the N-terminus.

The polypeptides may also be synthesized chemically, ribosomally in a cell free system, or ribosomally within a cell.

Utility and Administration

General Utility

The compounds of the present invention have been found to possess valuable pharmacological properties, and have been shown to effectively block the inflammatory effects of RANTES. Accordingly, they are useful for the treatment of asthma, allergic rhinitis, atopic dermatitis, atheroma/atheroschleosis, and rheumatoid arthritis. The compounds of the present invention have also been shown to inhibit HIV-1 infection in vitro.

Testing

The potential of the compounds for utility against HIV-1 is determined by the method, described in the following Examples. The potential of the compounds for utility against inflammatory effects is determined by methods well known to those skilled in the art.

General Administration

The polypeptides of this invention and their pharmaceutically acceptable salts, i.e., the active ingredient, are administered at a therapeutically effective dosage, i.e., that amount which, when administered to a mammal in need thereof, is sufficient to effect treatment, as described above. Administration of the polypeptides described herein can be via any of the accepted modes of administration for agents that serve similar utilities. As used herein, the terms "polypeptides of this invention", "polypeptides", "pharmaceutically acceptable salts of the polypeptides of the invention" and "active ingredient" are used interchangeably.

The level of the polypeptide in a formulation can vary within the full range employed by those skilled in the art, e.g., from about 0.01 percent weight (% w) to about 99.99% w of the polypeptide based on the total formulation and about 0.01% w to 99.99% w excipient More typically, the polypeptide will be present at a level of about 0.5% w to about 80% w.

While human dosage levels have yet to be optimized for the polypeptides of the invention, generally, a daily dose is from about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day. The amount of polypeptide administered will, of course, be dependent on the subject and disease state being treated, the severity of the affliction, the manner and schedule of administration and the judgment of the prescribing physician. Such use optimization is well within the ambit of those of ordinary skill in the art.

Administration can be via any accepted systemic or local route, for example, via parenteral, oral (particularly for infant formulations), intravenous, nasal, bronchial inhalation (i.e., aerosol formulation), transdermal or topical routes, in the form of solid, semi-solid or liquid or aerosol dosage forms, such as, for example, tablets, pills, capsules, powders, liquids, solutions, emulsion, injectables, suspensions, suppositories, aerosols or the like. The polypeptides of the invention can also be administered in sustained or controlled release dosage forms, including depot injections, osmotic pumps, pills, transdermal (including electrotransport) patches, and the like, for the prolonged administration of the polypeptide at a predetermined rate, preferably in unit dosage forms suitable for single administration of precise dosages. The compositions will include a conventional pharmaceutical carrier or excipient and a polypeptide of the invention and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Oral administration can be used to deliver the polypeptides of the invention using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, povidone, magnesium stearate, sodium saccharine, talcum, cellulose, croscarmellose sodium, glucose, gelatin, sucrose, magnesium carbonate, and the like. Such compositions take the form of solutions, suspensions, dispersible tablets, pills, capsules, powders, sustained release formulations and the like.

The compositions may take the form of a capsule, pill or tablet and thus the composition will contain, along with the active ingredient, a diluent such as lactose, sucrose, dicalcium phosphate, and the like; a disintegrant such as croscarmellose sodium, starch or derivatives thereof; a lubricant such as magnesium stearate and the like; and a binder such as a starch, polyvinylpyrrolidone, gum acacia, gelatin, cellulose and derivatives thereof, and the like.

Liquid pharmaceutically administrable compositions can, for example, be prepared by dissolving, dispersing, etc. a polypeptide of the invention (about 0.5% to about 20%) and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, etc. Actual methods of preparing such dosage forms are known, or will be apparent, to those skilled in this art; for example, see Remington's Pharmaceutical Sciences, Mack Publishing Company, Easton, Pa. The composition or formulation to be administered will, in any event, contain a quantity of the active ingredient in an amount effective to alleviate the symptoms of the subject being treated. For oral administration to infants, a liquid formulation (such as a syrup or suspension) is preferred.

For a solid dosage form containing liquid, the solution or suspension, in for example propylene carbonate, vegetable oils or triglycerides, is preferably encapsulated in a gelatin capsule. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active ingredient in vegetable oils, glycols, triglycerides, propylene glycol esters (e.g. propylene carbonate) and the like, and encapsulating these solutions or suspensions in hard or soft gelatin capsule shells.

In applying the polypeptides of this invention to treatment of the above conditions, administration of the active ingredients described herein are preferably administered parenterally. Parenteral administration is generally characterized by injection, either subcutaneously, intramuscularly or intravenously, and can include intradermal or intraperitoneal injections as well as intrasternal injection or infusion techniques. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, polyoxyethylene, sorbitan monolaurate, triethanolamine oleate, cyclodextrins, etc.

The polypeptides of the present invention can be administered parenterally, for example, by dissolving the polypeptide in a suitable solvent (such as water or saline) or incorporation in a liposomal formulation followed, by dispersal into an acceptable infusion fluid. A typical daily dose of a polypeptide of the invention can be administered by one infusion, or by a series of infusions spaced over periodic intervals. For parenteral administration there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents.

A more recently devised approach for parenteral administration employs the implantation of a slow-release or sustained-release system, such that a constant level of dosage is maintained. See, e.g., U.S. Pat. No. 3,710,795, which is hereby incorporated by reference.

The percentage of the active ingredient contained in such parental compositions is highly dependent on the specific nature thereof, as well as the activity of the polypeptide and the needs of the subject. However, percentages of active ingredient of 0.01% to 10% in solution are employable, and will be higher if the composition is a solid which will be subsequently diluted to the above percentages. Preferably the composition will comprise 0.02–8% of the active ingredient in solution.

Another method of administering the polypeptides of the invention utilizes both a bolus injection and a continuous infusion. This is a particularly preferred method when the therapeutic treatment is for the prevention of HIV-1 infection.

Aerosol administration is an effective means for delivering the polypeptides of the invention directly to the respiratory tract. Some of the advantages of this method are: 1) it circumvents the effects of enzymatic degradation, poor absorption from the gastrointestinal tract, or loss of the therapeutic agent due to the hepatic first-pass effect; 2) it administers active ingredients which would otherwise fail to reach their target sites in the respiratory tract due to their molecular size, charge or affinity to extra-pulmonary sites; 3) it provides for fast absorption into the body via the alveoli of the lungs; and 4) it avoids exposing other organ systems to the active ingredient, which is important where exposure might cause undesirable side effects. For these reasons, aerosol administration is particularly advantageous for treatment of asthma, local infections of the lung, and other diseases or disease conditions of the lung and respiratory tract.

There are three types of pharmaceutical inhalation devices, nebulizers inhalers, metered-dose inhalers and dry powder inhalers. Nebulizer devices produce a stream of high velocity air that causes the polypeptide (which has been formulated in a liquid form) to spray as a mist which is carried into the patient's respiratory tract. Metered-dose inhalers typically have the formulation packaged with a compressed gas and, upon actuation, discharge a measured amount of the polypeptide by compressed gas, thus affording a reliable method of administering a set amount of agent. Dry powder inhalers administer the polypeptide in the form of a free flowing powder that can be dispersed in the patient's air-stream during breathing by the device. In order to achieve a free flowing powder, the polypeptide is formulated with an excipient, such as lactose. A measured amount of the polypeptide is stored in a capsule form and is dispensed to the patient with each actuation. All of the above methods can be used for administering the present invention.

Pharmaceutical formulations based on liposomes are also suitable for use with the polypeptides of this invention. The benefits of liposomes are believed to be related to favorable changes in tissue distribution and pharmacokinetic parameters that result from liposome entrapment of drugs, and may be applied to the polypeptides of the present invention by those skilled in the art. Controlled release liposomal liquid pharmaceutical formulations for injection or oral administration can also be used.

For systemic administration via suppository, traditional binders and carriers include, for example, polyethylene glycols or triglycerides, for example PEG 1000 (96%) and PEG 4000 (4%). Such suppositories may be formed from mixtures containing the active ingredient in the range of from about 0.5 w/w % to about 10 w/w %; preferably from about 1 w/w % to about 2 w/w %.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of n-Hexanoyl-[Gly$^1$]RANTES (2-33) (SEQ ID NO:6)

[Gly$^1$]RANTES (2-33) was synthesized by solid phase peptide synthesis on a thioester producing resin, and then chemically modified at the N-terminus by direct coupling of n-hexanoic acid to the resin. The product was cleaved with hydrogen fluoride and purified by reverse-phase chromatography, to yield n-hexanoyl-[Gly$^1$]RANTES (2-33), a compound of formula (4).

Example 2

Preparation of RANTES (34-68)

RANTES (34-68) was synthesized by conventional solid phase peptide synthesis on a Boc-Ser-$OCH_2$-Pam-resin followed by cleaving with hydrogen fluoride. The product was purified by reverse-phase preparative HPLC, to yield RANTES (34-68) or Cys$^{34}$-RANTES (35-68)—COOH, a compound of formula (5). Observed mass=4096.73 Da; Calculated mass=4097.8 Da (average).

Example 3

Preparation of n-Hexanoyl-[Gly$^1$]RANTES (2-68) (SEQ ID NO:5)

n-Hexanoyl-[Gly$^1$]RANTES (2-68) was prepared by chemically ligating equimolar amounts of the compounds of formula (4) and (5) from Examples 1 and 2 (22 mg each) in 6M guanidine hydrochloride, 200 mM of sodium phosphate, 30 mM L-methionine, at pH 7 containing 1% v/v thiophenol. After 20 hours the reaction was complete, and the product was purified by reverse-phase semi-preparative HPLC and lyophilization, to yield 22.6 mg of reduced n-hexanoyl-[Gly$^1$]RANTES (2-68).

Folding and formation of the disulfides was carried out in 8mM cysteine, 1 mM cystine, 2 M guanidine hydrochloride, 100 mM TRIS pH 8.00 at a protein concentration of 1 mg/ml. Gentle stirring at room temperature resulted in quantitative folding, and purification by reverse-phase semi-preparative HPLC and lyophilization yielded 12.6 mg of folded n-hexanoyl-[Gly$^1$]RANTES (2-68). Observed mass=7915.09 Da; Calculated mass=7915.2 Da (average).

Example 4

Preparation of n-Nonanoyl-RANTES (2-68) (SEQ ID NO:2)

The peptide, n-nonanoyl-RANTES (2-68) was synthesized using the in situ neutralization/HBTU (Spectrum Quality Products, Inc., Gardena, Calif.) activation protocols for Boc chemistry solid phase peptide synthesis as described in Schnölzer, et al., *Int. J. Pept. Protein Res.* 40:180–193 (1992). Boc-amino acids were purchased from Peptide Institute, Inc. (Osaka, Japan). Peptide α-carboxylates were assembled on a Boc-Ser-$OCH_2$-Pam resin (PE Applied Biosystems, Foster City, Calif.) and the peptide α-thiocarboxylates on a thioester generating resin, as described in Hojo, et al., *Bull. Chem. Soc. Jpn.* 64, 111–117 (1991). The N-terminal modifications were incorporated by on-resin reaction of RANTES (2-33) with the preformed n-nonanoic acid to give n-nonanoyl-RANTES (2-33) thioester. Peptides were cleaved from the resin using hydrogen fluoride containing 5% v/v p-cresol (FLUKA, Buehs, Switzerland) for 1 hour at 0° C. and purified by reversed-phase HPLC (VYDAC, Inc., Hesperia, Calif.) with a linear gradient of acetonitrile versus water con 0.1% trifluoroacetic acid to yield n-nonanoyl-RANTES (2-33)-S—Ac-Leu (SEQ ID NO:3).

Native chemical ligation (Dawson, et al., *Science* 266 : 776–779 (1994)) of the fully unprotected peptide segment with RANTES (34-68) (SEQ ID: 4) in aqueous buffer gave the full length polypeptide in reduced form (n-nonanoyl-RANTES (2-68) reduced)), which was folded in aqueous buffer and purified by reversed-phase HPLC . The folded n-nonanoyl-RANTES (2-68) (8.4 mg) was homogeneous on HPLC. Observed mass=7899.96 Da; Calculated mass=7900.21 Da (average).

Example 5

Preparation of n-Hexyl-[Gly$^1$]RANTES (2-68) (SEQ ID NO:5)

RANTES (2-3) SEQ ID NO:3 by solid phase peptide synthesis on a thioester producing resin, and then chemically modified at the N-terminus by direct coupling of bromoacetic acid to the resin followed by n-hexylamine. The product was cleaved with hydrogen fluoride and purified by reverse-phase chromatography, to yield n-hexyl-[Gly$^1$]RANTES (2-33) (SEQ ID NO:6).

This material was chemically ligated with a compound of formula (5) as shown in Example 3 above, to give n-hexyl-[Gly$^1$]RANTES (2-68) (5.4 mg). Observed mass=7901.36 Da; Calculated mass=7901.2 Da (average).

Example 6

Preparation of n-Nonyl-RANTES (2-68) SEQ ID NO:2

As shown in FIG. 1, RANTES (2-33) (SEQ ID NO:3) was synthesized by solid phase peptide synthesis on a thioester producing resin, and then chemically modified at the N-terminus by direct coupling of 1-bromo-nonane to the resin. The product was cleaved with hydrogen fluoride and purified by reverse-phase chromatography, to yield n-nonyl-RANTES (2-33)-S—Ac-Leu.

This material was chemically ligated with a compound of formula (5) as shown in Example 3 above, to give n-nonyl-RANTES (2-68) reduced, which was then folded and purified as shown in Example 3 above to give folded n-nonyl-RANTES (2-68) (5.8 mg). Observed mass=7886.16 Da; Calculated mass=7886.2 Da (average).

Example 7

By using the above methods the following compounds were similarly prepared:

n-pentyloxy-[Gly$^1$]RANTES (2-68); (SEQ ID NO:5)

3-pentyloxypropan-1-oyl-RANTES (2-68) (SEQ ID NO:2); and non-2-en-1-ylRANTES (2-68) (SEQ ID NO:2).

Example 8

Preparation of AOP-RANTES (2-68)

The peptides, aminooxypentane-RANTES (2-68) ("AOP-RANTES (2-68) (SEQ ID NO:2)") was synthesized using the in situ neutralization/HBTU (Spectrum Quality Products, Inc., Gardena, Calif.) activation protocols for Boc chemistry solid phase peptide synthesis as described in Schnölzer, et al., *Int. J. Pept. Protein Res.* 40:180–193 (1992). Boc-amino acids were purchased from Peptide Institute, Inc. (Osaka, Japan). Peptide α-carboxylates were assembled on a Boc-Ser-OCH$_2$-Pam resin (PE Applied Biosystems, Foster City, Calif.) and the peptide α-thiocarboxylates on a thioester generating resin, as described in Hojo, et al., *Bull. Chem. Soc. Jpn.* 64, 111–117 (1991). The N-terminal modifications were incorporated by on-resin reaction of RANTES (2-33) (SEQ ID NO:3) with the preformed oximen n-pentyl-O—N=CHCOOH as the last step in the chain assembly to give AOP-RANTES (2-33) (SEQ ID NO:3). Pepetides were cleaved from the resin using hydrogen fluoride containing 5% v/v p-Cresol (FLUKA, Buehs, Switzerland) for 1 hour at 0° C. and purified by reversed-phase HPLC (VYDAC, Inc., Hesperia, Calif.) with a linear gradient of acetonitrile versus water containing 0.1% trifluoroacetic acid. Native chemical ligation (Dawson, et al., *Science* 266:776–779 (1994)) of the fully unprotected peptide segments AOP-RANTES (2-33) thioester with RANTES (34-68) (SEQ ID NO:4) in aqueous buffer gave the full length polypeptide in reduced form, which was folded in aqueous buffer and purified by reversed-phase HPLC. The folded AOP-RANTES was homogeneous on HPLC and gave a molecular mass of 7901.2±0.8 Daltons ("Da") on electrospray ionization mass spectroscopy (calculated average isotope composition 7901.2 Da

Example 9

Chemotaxis Assays

Human peripheral blood leukocytes are isolated from normal donors according to established protocols for purification of monocytes, T lymphocytes and neutrophils. A panel of CC and CXC chemokine receptor-expressing test cells is constructed and evaluated following exposure to serial dilutions of individual compounds of the present invention. Synthetic native RANTES (SEQ ID NO:1) a native CXC-chemokine ("SDF-1α"), MPAV and MPBV are used as controls. The panel of cells represent human kidney embryonic epithelial ("HEK") 293 cells transfected with expression cassettes encoding various chemokine receptors including CXCR4/Fusion/LESTR, CCR3, CCR5, CXC4 (these cells are available from various commercial and/or academic sources or can be prepared following standard protocols). Leukocyte migration relative to the transfected HEK 293 cells is evaluated using a 48-well microchamber, migration of the receptor transfected HEK 293 cells also is assessed by the 48-well microchamber technique with the polycarbonate filters (10 μm pore-size) precoated with Collagen type I (Collaborative Biomedical Products, Bedford, Mass.) (Neote, et al., *supra*; Risau, et al., *Nature* 387:671–674 (1997); Angiololo, et al., *Annals NY Acad. Sci.* 795:158–167 (1996); Friedlander, et al., *Science* 870:1500–1502 (1995)). The results are expressed as the chemotaxis index ("CI") representing the fold increase in the cell migration induced by stimuli versus control medium. All experiments are performed at least two times. The statistical significance of the difference between migration in response to stimuli and control are accessed by Student's T test.

Example 10

Receptor Binding Assays

Receptor binding assays are performed using a single concentration of $^{125}$I labeled chemokines in the presence of increasing concentrations of unlabeled ligands following standard protocols. The binding data are analyzed, for example, with a computer program such as LIGAND (P.Munson, Division of Computer Research and Technology, NIH, Bethesda, Md.). The binding data are subjected to Scatchard plots analysis with both "one site" and "two site" models compared to native leukocytes or the panel of receptor-transfected HEK 293 cells expressing CXCR4, CCR3, CCR5 or CXC4. The rate of competition for binding by unlabeled ligands is calculated with the following formula: % inhibition=1–(Binding in the presence of unlabeled chemokine/binding in the presence of medium alone)×100.

Example 11

HIV-1 Inhibition Assays

A. Chemokine receptors act as co-factors for HIV-1 entry into CD4$^+$ cells. The CC chemokines MIP-1α, MIP-1β, RANTES and eotaxin can suppress some strains of HIV replication in primary peripheral blood mononuclear cells ("PBMCs") and chemokine receptor transfected cell lines. The viral produced chemokine vMIP-1 inhibits some primary non-syncytium inducing (NSI) HIV strains when co-transfected with the NSI strain HIV-1 co-receptor CCR5. CCR3 is the predominant chemokine receptor through which eotaxin, RANTES and other CC chemokines activate eosinophils. RANTES (SEQ ID NO:2) and MIP-1α also can utilize the CCR1 receptor that is expressed on eosinophils. In addition, synthetic N-terminal variants of CC (e.g. Met-RANTES) and CXC (e.g. IL-8) chemokines function as receptor antagonists on eosinophils and neutrophils, whereas the native structures do not Similarly, the CXC chemokine SDF-1α is a potent chemoattractant for leukocytes through activation of the receptor CXCR4/Fusin/LESTR, which is a fusion co-factor for the entry of HIV-1. CXCR4 mediated HIV-1 fusion can be inhibited in some cells by SDF-1α. Thus, despite the sequence similarities between certain chemokines of the same family, the binding and antagonist/agonist properties for HIV infection vary significantly.

Polypeptides of the invention are screened for receptor usage, inhibition of HIV infection, potency and breadth of activity against HIV infection, induction of calcium mobilization and angiogenesis. The assays are used to evaluate suppression of HIV-1 infection/replication in U87/CD4 cells (a human glioma cell line) expressing HIV-1 co-receptors and also in PBMCs.

The receptor-transfected U87/CD4 cells are obtainable by transfecting cells with an expression cassette encoding the respective receptors following standard protocols. The cells are maintained in Dulbecco's Minimal Essential Medium containing 10% fetal calf serum ("FCS"), glutamine, antibiotics, 1 µg/ml puromycin (Sigma Chemicals) and 300 µg/ml neomycin (G418; Sigma) and split twice a week. PBMCs are isolated from healthy blood donors by Ficoll-Hypaque centrifugation, then stimulated for 2–3 days with phytohemagglutinin ("PHA") (5 µg/ml) and IL-2 (100 U/ml) (Simmons, et al., *J. Virol.* 70:8355–8360 (1996)). $CD4^+$ T-cells are purified from the activated PBMCs by positive selection using anti-CD4 immunomagnetic beads (DYNAL Inc.), screened for CCR-5 defective alleles, and cells from allele defective or wild-type donors used depending on the assay. HIV isolates are obtainable from various sources including the NIAID HIV-1 Antigenic Variation study, or from similar programs organized by the US Department of Defense or the World Health Organization. Phenotypes of test viruses are tested by their ability to form syncytia ("SI") in MT-2 cells that are cultured in RPMI 1640 medium containing 10% FCS, glutamine and antibiotics, and split twice a week. Human CC-Chemokines MIP-1α, MIP-1β and RANTES, and CXC-chemokines SDF-1α stocks are compared for purity and potency.

B. Assay for Inhibition of HIV Infection

Compounds of the present invention are tested against a panel of U87/CD4 cells stably expressing either CCR3, CCR5, CXC4 or CXCR4 receptors exposed to HIV-1/NSI strains SL-2 and SF 162 (macrophage-tropic strains that utilize the RANTES, MIP-1α and MIP-1β receptor CCR5 to gain entry into $CD4^+$ cells) and the dual-tropic syncytium inducing strains 89.6 and 2028 (syncytium inducing dual tropic strains that can use CXCR4 and CCR3 in addition to CCR5 for entry). Lymphocytes and $CD4^+$ T-Cells from donors also are tested. Serial concentrations ranging from 0 to 500 nM of the cross-over proteins are used. RANTES, MPBA, MPBV and SDF-1α are used as controls. Inhibition of HIV infection is reported as a percentage of infection relative to modular protein and control concentrations.

Purified lymphocytes are stimulated with PHA (0.5 µg/ml) and cultured for 2–3 days at 2×106/ml in medium containing IL-2 (Boeringer-Mannheim, 20 U/ml) before being used in infection assays. Cells are pre-treated with appropriate concentrations of chemokines for 30 minutes at 37° C. Approximately 400–1000 tissue culture infectious doses ("TCIDs") of virus are added. The cells are washed 4 times and resuspended in an appropriate volume of media containing IL-2 and relevant chemokine at the appropriate concentration. Cells are fed every 3 days with fresh medium contain IL-2 and chemokine. From days 3 through 7 post-infection, the cultures are examined microscopically for syncytium formation and the supernatant analyzed for p24 antigen production using an enzyme linked immunoabsorbent assay ("ELISA") (McKnight, et al., *Virology* 201:8–18 (1994); and Mosier, et al., *Science* 260:689–692 (1993)). Inhibitory doses a calculated relative to the final concentration of chemokine in the culture on day 0. Virus-production in the absence of chemokine is designated as 100%, and the ratios of p24 antigen production in chemokine—containing cultures calculated relative to this percentage. The chemokine concentrations (pg/ml) causing 50% and 900% reduction in p24 antigen production are determined by linear regression analysis. If the appropriate degree of inhibition is not achieved at the highest or lowest chemoline concentration, a value of >or< is recorded.

Virus infectivity on the receptor expressing U87/CD4 cells is assessed by focus-forming units (FFU) (Simmons, et al, *Science* 276:276–279(1997)). The FFU for viruses using more than one co-receptor is assessed separately for each appropriate co-receptor expressing U87/CD4 cell type. Cells are seeded into 48 well trays at 1×104 cells/well overnight. The cells are then pre-treated for 30 minutes at 37° C. with appropriate concentrations of chemokine in 75 µl. 100 FFU of each virus in 75 µl is added and incubated for 3 hours at 37° C. Cells are washed 3 times and 500 µl of medium containing the appropriate chemokine at the correct concentration is added. After 5 days the cells are fixed for 10 minutes in cold acetone:methanol (1:1) and analyzed for p24 antigen production. Stand potency of cross-over chemokines against HIV infection The breadth and potency of the inhibitory actions of the compounds of the present invention are tested against native CC-Chemokines (MIP-1α, MIP-1β and RANTES) for M-tropic primary isolates of HIV-1, and against a native CXC-Chemokine (SDF-1α) for T-tropic isolates in mitogen-stimulated primary $CD4^+$ T-Cells. The compounds are evaluated for their potency and spectrum of agonistic activity against HIV-1 strains relative to the native CC- and CXC-chemokines to identify the most active inhibitor of HIV-1 replication and the best template for therapeutic development. The properties and activities of M-Tropic and T-tropic primary HIV-1 isolates are recorded and compared to inhibition of infection by exposure to the cross-over chemokines relative to the HIV isolate designation, genetic subtype, and phenotype determined by ability of an isolate to form ("SI") or not form ("NSI") syncytia in MT-2 cells, the ability of an isolate to replicate efficiently in activated $CD4^+$ T-Cells from individuals homozygous for either wild-type or delta-32 CCR5 alleles, and the ability of an isolate to replicate in U87/CD4 cells stably expressing either CCR5 or CXCR4. The median $ID_{50}$ and $ID_{90}$ values (ng/ml) are calculated for each sample. A Value of > indicates that 50% or 90% inhibition is not achieved at a chemokine concentration of the highest tested in any experiment. The means from two independent experiments are compared. FACS analysis of CCR5 and CXCR4 receptor expression levels, and/or competitive inhibition assay of the compounds of the present invention and receptor down-regulation also may be tested following standard protocols (Wu, et al., *J. Exp. Med.* 185:168–169(1997); and Trkola, et al., *Nature* 384:184–186 (1996)).

Example 12

Assay for Measuring Changes in Intracellular Calcium Concentration ($[Ca^{2+}]$)

Calcium mobilization is indicative of receptor binding. The compounds of the present invention are assayed for calcium mobilization in purified neutrophils and eosinophils following standard protocols (Jose, et al., *J. Exp. Med.* 179:881–887 (1994)). Purified neutrophils or eosinophils are incubated with fura-2 acetoxymethyl ester (1–2.5 μM), washed 3 times in 10 mM phosphate buffered saline ("PBS") (without $Ca^{2+}/Mg^{2+}$) and 0.1% bovine serum albumin ("BSA") (200×g, 8 min), and finally resuspended at 2×106 cells/ml in 10 mM PBS (without $Ca^{2+}/Mg^{2+}$), 0.25% BSA, 10 mM HEPES, and 10 mM glucose. Aliquots of cells are placed in quartz cuvettes and the external $Ca^{2+}$ concentration adjusted to 1 mM with $CaCl_2$ Changes in fluorescence are measured at 37° C. using a fluorescence spectrophotometer at excitation wavelengths 340 nm and 3.80 nm and emission wavelength 510 nm. [$Ca^{2+}$] levels are calculated using the ratio of the two fluorescence readings and a K for $Ca^{2+}$ at 37° C. of 224 nM.

Example 13

CAM Assay for Angiogenic Activity

Angiogenic activities of compounds of the present invention are evaluated by the chick chorioallantoic membrane (CAM) assay (Oikawa, et al., *Cancer Lett.* 59:57–66 (1991)). Native chemokines are used as controls. Fertilized Plymouth Rock Leghorn eggs are incubated at 37° C. in a humidified atmosphere (relative humidity, approx. 70%). Test samples are dissolved in sterile distilled water or PBS. Sterilized sample solution is mixed with an equal volume of autoclaved 2% methylcellulose. Additional controls are prepared with vehicle only (1% methylcellulose solution). 20 μl of the sample solution is dropped on parafilm and dried up. The methylcellulose disks are stripped off from the parafilm and placed on a CAM of a 10 or 11 day old chick embryo. After 3 days, the CAMs are observed by means of an Olympus stereoscope. A 20% fat emulsion (Intralipos 20%, Midori-Juji, Osaka, Japan) is injected into the CAM to increase the contrast between blood and surrounding tissues (Danesi, et al., *Clin. Cancer Research* 3:265–272(1997)). The CAMs are photographed for evaluation of angiogenic response. Angiogenic responses are graded as negative, positive or unclear on the basis of infiltration of blood vessels into the area of the implanted methylcellulose disk by different observers.

Example 14

AOP-RANTES Inhibits HIV-1 Replication In Vivo and In Vitro

Primary macrophage-tropic isolates of HIV-1 (R5 viruses) use CCR5 as a co-receptor for virus entry into targetcells. CCR5 binds RANTES, MIP-1α, and MIP-1β, and each of these chemokines can block virus entry into T cells at relatively high concentrations. N-terminal modifications of RANTES with higher affinity for CCR5 binding have been tested for inhibition of virus entry and replication in both T cells and macrophages in vitro. In addition, in vivo tests of the efficacy of these antagonists have been performed in SCID mice repopulated with human peripheral blood mononuclear cells (the "hu-PBL-SCID" model, described in Mosier, et al., *Nature* (London) 335:256–259 (1988) and Mosier, et al., *Science* 251:791–794 (1991)). AOP-RANTES (SEQ ID NO:2) is an effective inhibitor of M-tropic R5 virus replication in vitro at nanomolar concentration. The same compound substantially reduces virus levels when administered to hu-PBL-SCID mice just prior to virus infection and continuously for the ensuing week. Virus rebounds once treatment is stopped, but the recovered virus shows no mutations in the V3 region and has not altered co-receptor usage. First generation chemokine antagonists thus show antiviral efficacy in an animal model, and this antiviral effect may not select for viral variants with altered co-receptor utilization.

AOP-RANTES Inhibits HIV-1 Replication in hu-PBL-SCID Mice

Hu-PBL-SCID mice were generated by injection of 20×10⁶ PBMCs from an EBV-seronegative donor on day −14 or −15, using methods described in Mosier, *Adv. Immunol.* 63:79–125 (1996), Picchio, et al., *J. Virol.* 71:7124–7127 (1997), and Picchio, et al., *J. Virol.* 72:2002–2009 (1998). The mice were divided into groups of four mice each. Group 1 received implantation of an Alzet 2001 mini-osmotic pump (ALZA Pharmaceuticals, Palo Alto, Calif.) containing 2.5 mg/ml of AOP-RANTES (delivered at a rate of 1 μl per hour for a minimum of 200 hours). Group 2 received implantation of a similar Alzet pump containing 2.5 mg/ml of BSA. The Alzet pumps were implanted subcutaneously on day −1 (14 days after the SCID mice were reconstituted). Thus, on day −1, delivery of AOP-RANTES began for mice in Group 1. On the following day (day 0), the Group 1 mice were given a single bolus injection of 1 mg AOP-RANTES and the Group 2 mice were given a single bolus injection of 1 mg BSA. One hour later, all mice were challenged with 1000 TCIDs of the M-tropic 242 HIV-1 isolate (Chesebro, et al., supra and Speck, et al., supra).

Virus infection was monitored by plasmid HIV RNA levels, which were determined using the Roche Amplicor HIV Monitor assay, a quantitative PCR determination with a limit of detection of 200 copies/ml. One AOP-RANTES mouse died on day 6 of a surgical complication of pump replacement. Plasma samples were obtained from all mice on day 7 (7 days after infection with HIV-1) and plasma HIV-1 RNA copy number measured on days 7 and 14 (after infection). Plasma RNA levels 200 are undetectable with the Roche assay, so two mice (#1 and #2) shown as 200 copies/ml on day 7 after infection had undetectable viral RNA levels. The reduction in plasma virus RNA levels by AOP-RANTES at day 7 after infection were highly significant (p<0.001).

Plasma AOP-RANTES levels on day 7 were determined with a human RANTES ELISA kit (R&D). Plasma concentrations of AOP-RANTES in the range of 1–5 ng/ml suggest that plasma clearance is more rapid than Alzet pump delivery rate.

Figure 2:
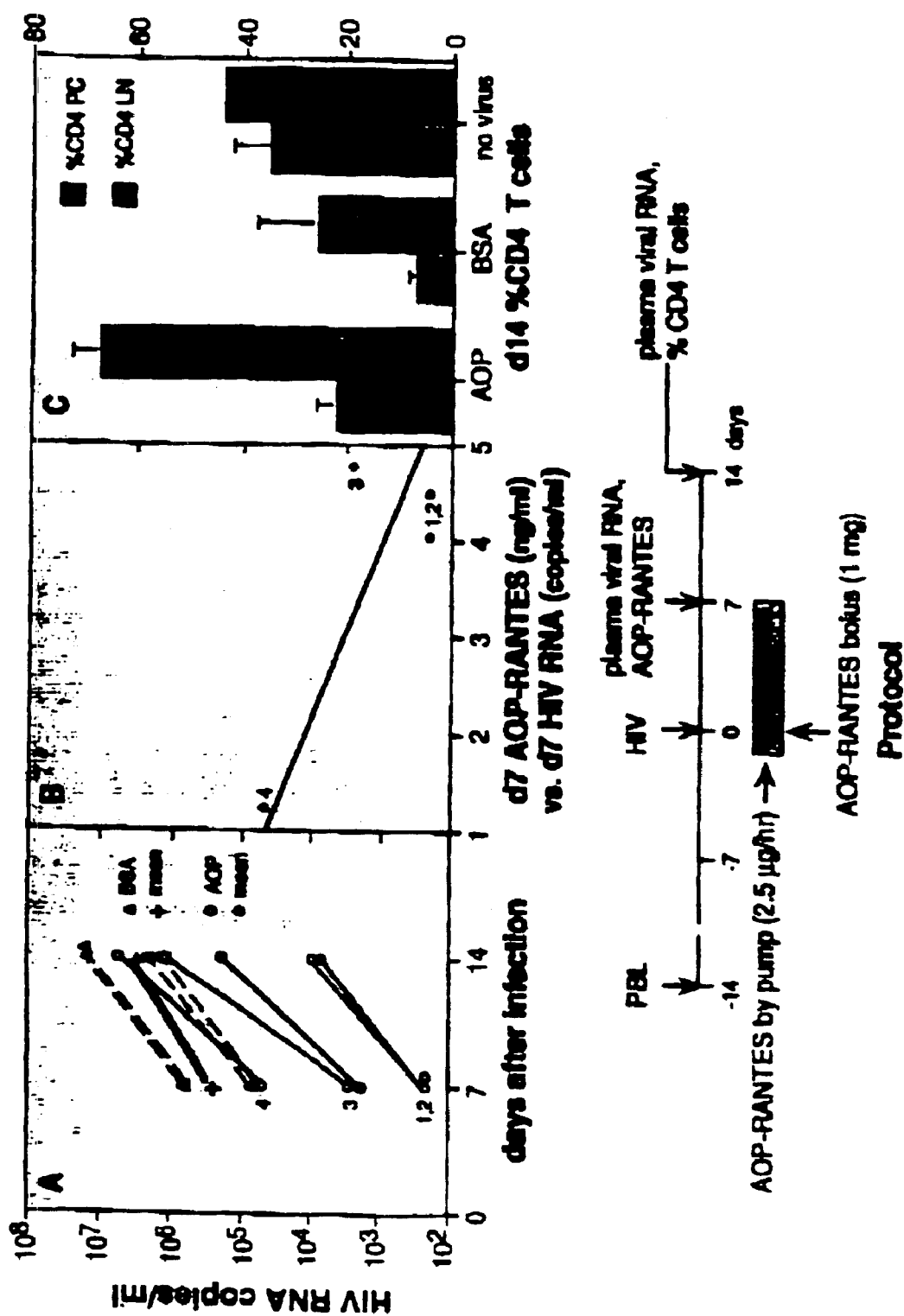
FIG. 2 shows the effect of AOP-RANTES treatment on HIV infection in hu-PBL-SCID mice.

At the final time point, mice from each group were sacrificed for determination of the numbers of human CD3, CD4, CD8, and CD45-positive cells in two sites, the peritoneal cavity site of cell injection, and local lymph nodes ("LN") draining the peritoneal cavity. The frequency of human cell types was determined by staining with fluorochrome-labeled antibodies followed by fixation and flow cytometric analysis, as described in Picchio, et al., *J. Virol.* 72:2002–2009 (1998) and Picchio, et al., *J. Virol.* 71:7124–7127 (1997). The %CD4 T cells was measured 14 days after infection. This is illustrated in FIG. 2.

After cessation of AOP-RANTES treatment, virus bounced back in all mice. Infection was delayed and CD4 T cells spared (at least temporarily) by AOP-RANTES treatment, but virus infection was not blocked.

AOP-RANTES has now been shown to be non-toxic and to significantly delay HIV-1 virus infection. Approximately 50 mg/kg of neutralizing antibody is required to block infection of the mice.

Example 15

Figure 4:
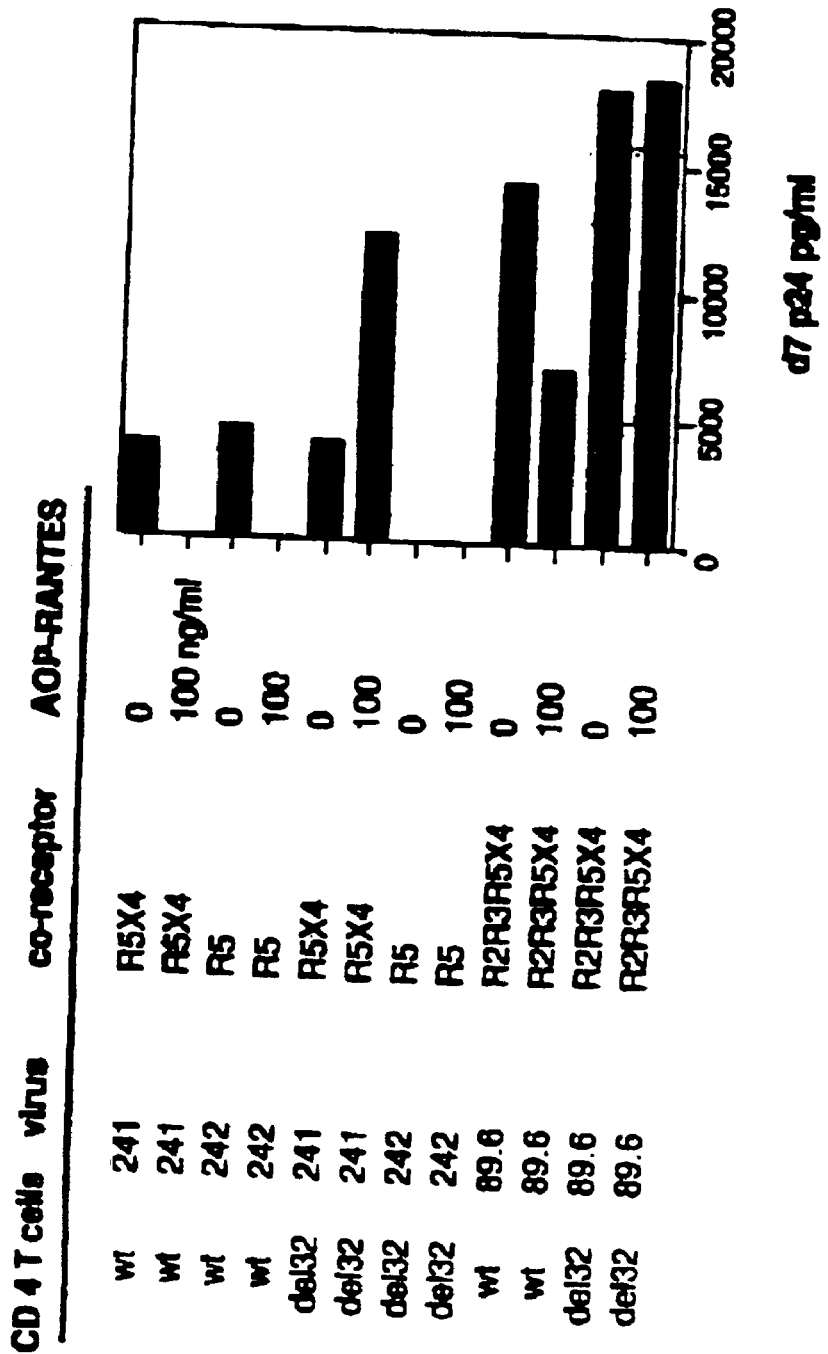
FIG. 4 shows the in vitro effect of AOP-RANTES treatment on R5 viruses.

In Vitro assays to Determine Inhibitory Effects of AOP-RANTES on Different HIV-1 Viruses In vitro experiments have concentrated on the inhibitory effects of AOP-RANTES (SEQ ID NO:2) on dual-tropic viruses that can use other co-receptors in addition to CCR5. These in vitro experiments involved use of a p24 virus replication assay as described in Mosier, et al., *supra*. Briefly, culture media was sampled at day 7 post-infection with the relevant HIV-1 isolate, and p24 was measured in pg/ml via an ELISA assay. The results are shown in FIG. 4, which shows that AOP-RANTES treatment in vitro inhibits R5 viruses but can enhance replication by R5X4 viruses in a CCR5-independent manner. Purified CD4 T cells were activated with PHA (and not IL-2) for 3 days prior to infection with HIV-1 242, 241 or the dual tropic 89.6 isolate. CD4 T cells were derived from either a normal donor (wild type "wt") or a donor homozygous for the 32 bp deletion in the CCR5 gene and thus having no expression of CCR5 on the cell surface ("del32") (as described in Picchio, et al., *J. Virol.* 71:7124–7127 (1997)).

As shown in FIG. 4, three different HIV-1 viruses were used: 241, 242, and 89.6. 89.6 is a dual-tropic HIV-1 isolate that uses multiple chemokine receptors, CCR2, CCR3, CCR5 and CXCR4, and is designated R2R3R5X4. Replication of HIV-1 242 in del32 CD4 T cells was enhanced by AOP-RANTES, but replication of HIV-1 89.6 in these T cells was unchanged by AOP-RANTES, as shown in FIG. 4.

All M-tropic viruses (R5 viruses) that use CCR5 only are efficiently inhibited. The dual tropic virus 241 is enhanced by some concentrations of AOP-RANTES when infection is measured on whole PBMCs, but is inhibited with purified CD4 T cells are the targets for infection. 241 infection was also enhanced by AOP-RANTES on purified CD4 T cells from CCR5 null (del32/del32) donors, suggesting some activity via other chemokine receptors. The dual-tropic 89.6 isolate that uses CCR2b, CCR3, and CSCR4 as well as CCR5 was inhibited about 50% by AOP-RANTES. Primary isolates of dual-tropic viruses from patients were inhibited between 80–90%. As might be expected, it appears that each dual-tropic virus isolate uses CCR5 to a greater or lesser extent Adding AOP-RANTES to a mixture of cell types can elicit strange responses, and its ability to trigger other CC receptors needs to be defined.

Example 16

Figure 5:
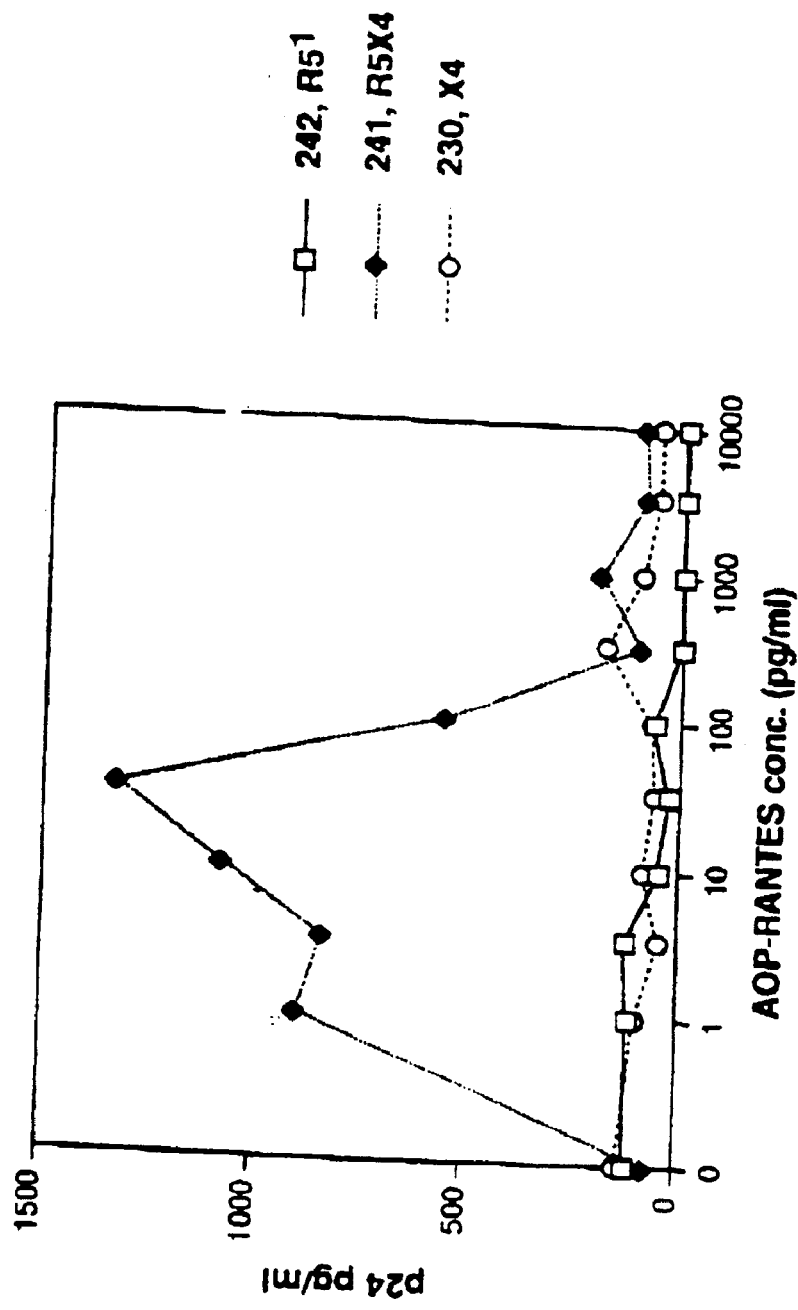
FIG. 5 depicts the effect of AOP-RANTES on HIV-1 infection in PBMC cultures.

Low Concentrations of AOP-RANTES Can Enhance Replication of Dual-Tropic HIV-1 in PBMC Cultures from Selected Donors Isolated PBMCs activated with PHA and IL-2 were infected with either HIV-1 242, 241 or 230 (see FIGS. 3 and 5) and viral replication monitored by p24 ELISA assay at days 4–18 of culture. Data in FIG. 5 are from day 11. Three independent PBMC donors (all CCR5 wt/wt) gave similar results as shown here, but other donors showed less enhancement of 241 replication, or even partial inhibition (See FIG. 4 where AOP-RANTES (SEQ ID NO:2) treatment of isolated CD4 T cells in vitro inhibits RS viruses but can enhance R5X4 viruses in a CCR5-independent manner).

Example 17

V3 Sequences of the Macrophage-tropic, CCR5 Using HIV-1 Molecular Clone Used in These Experiments, and Virus Recovered from Hu-PBL-SCID Mice After AOP-RANTES Treatment HIV-1 Clone 242 originated from B. Chesebro, and has the sequence indicated in FIG. 3 (SEQ ID NO:8). The 242 virus pool used in these experiments has a point mutation that resulted in a R to H change at position 21 (SEQ ID NO:9). Virus recovered from all AOP-RANTES-treated mice as well as control mice retained the 242/H V3 (SEQ ID NO:9) sequence.

Examples 14–17 shows that AOP-RANTES (SEQ ID NO:2) has no effect on T-Tropic, X4 virus replication. Further, AOP-RANTES may inhibit or enhance Dual-Tropic R5X4 virus replication in vitro. Enhancement (when it occurs) is virus and donor dependent, occurs at low doses of AOP-RANTES, and can occur in cells from CCR5-null (del320 donors. AOP-RANTES is non-toxic in vivo and is able to delay but not prevent infection with an M-tropic R5 isolate. No selection for V3 mutation is observed (in contrast to the rapid selection for escape mutations induced by antibody treatment in this model).

Example 18

N-nonanoyl-RANTES (2-68) Inhibits HIV-1 Replication in hu-PBL-SCID Mice

Fifteen SCID mice were reconstituted with $20 \times 10^6$ peripheral blood mononuclear cells from an EBV-seronegative donor on day −14, using methods described in Mosier, *Adv. Immunol.* 63:79–125 (1996), Picchio, et al., *J. Virol.* 71:7124–7127 (1997), and Picchio, et al., *J. Virol.* 72:2002–2009 (1998). The mice were divided into three groups of five mice each. Group 1 received no additional treatment. Group 2 received implantation of an Alzet 2001 mini-osmotic pump containing 500 μg of n-nonanoyl-RANTES (2-68) (SEQ ID NO:2) delivered at a rate of 1 μl per hour for a minimum of 200 hours). Group 3 received implantation of a similar Alzet pump containing 500 μg of BSA. The Alzet pumps were implanted subcutaneously on day −1 (13 days after the SCID mice were reconstituted). Thus, on day −1, delivery of n-nonanoyl-RANTES (2-68) began for mice in Group 2. On day 0, all 15 mice were infected with 1000 TCIDs of HIV-1 242, an isolate described in Chesebro, et al., supra, and Speck, et al., supra. Mice in group 2 received an intraperitoneal injection of 1 mg n-nonanoyl-RANTES (2-68) one hour prior to virus injection. N-nonanoyl-RANTES (2-68), was suspended in saline solution and heated to 37° C.

Virus infection was monitored by plasmid HIV RNA levels, which were determined using the Roche Amplico HIV Monitor assay, a quantitative PCR determination with a limit of detection of 200 copies/ml. Plasma samples were obtained from all mice on day 7 (7 days after infection with HIV-1, 8 days after implantation of Alzet pumps in Groups 2 and 3), on day 14 (14 days after infection), and day 28 (28 days after infection). At the final time point, 3 of the 5 mice from each group were sacrificed for determination of the numbers of human CD3, CD4, CD8, and CD45-positive cells in two sites, the peritoneal cavity site of cell injection, and local lymph nodes ("LN") draining the peritoneal cavity. The frequency of human cell types was determined by staining with fluorochrome-labeled antibodies followed by fixation and flow cytometric analysis, as described in Picchio, et al., *J. Virol.* 72:2002–2009 (1998) and Picchio, et al., *J. Virol.* 71:7124–7127 (1997).

Figure 6:
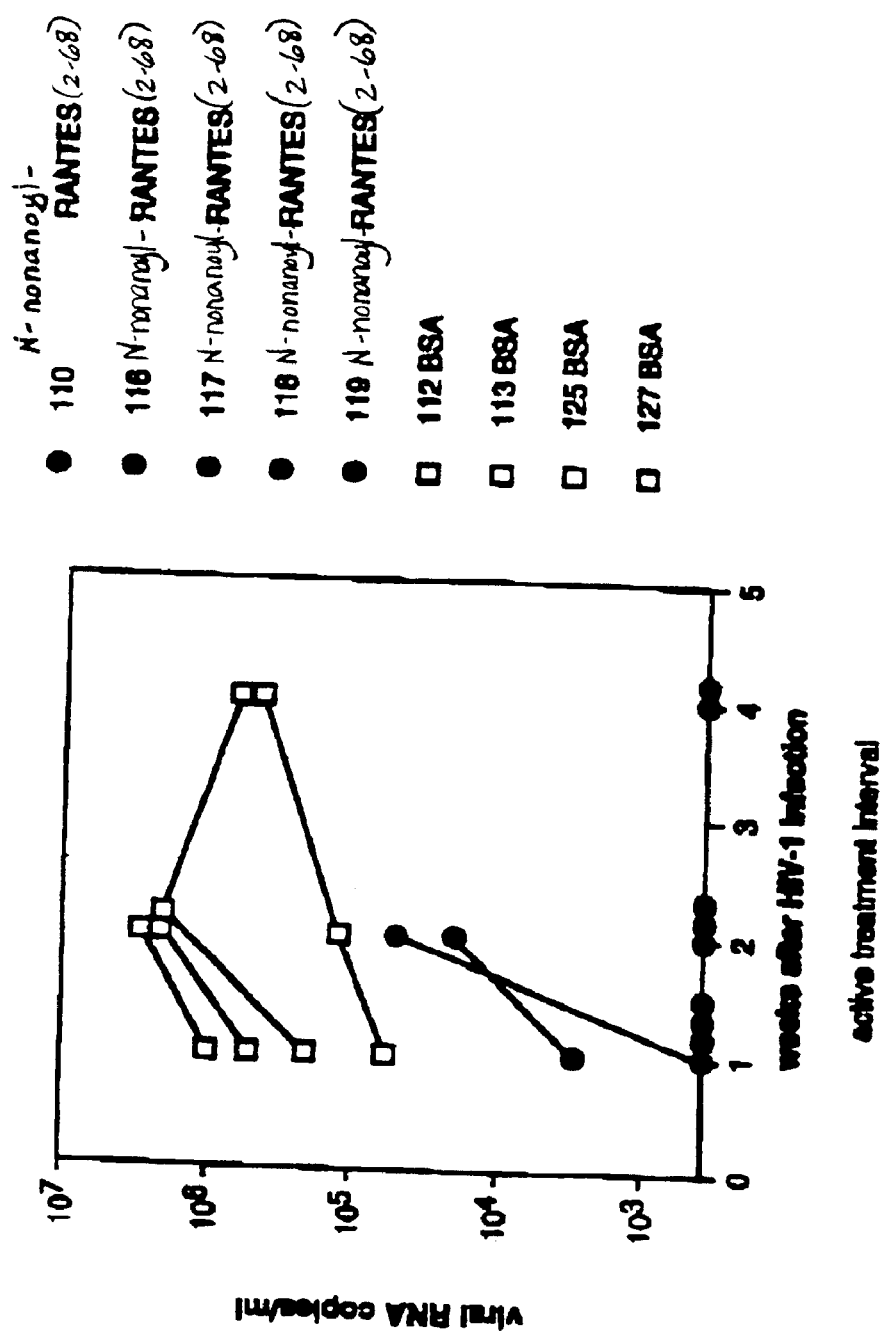
FIG. 6 shows the effect of n-nonanoyl-RANTES (2-68) (SEQ ID NO:2) on HIV-1 infection.

Results for HIV RNA levels (in copies/ml plasma) are generally shown in FIG. 6 as log-trasformed numbers. Log transformation is appropriate because viral replication is an exponential process, and small differences in viral load (e.g., <half $\log_{10}$) are insignificant Cell recovery is expressed as a percentage of total recovered cells, and CD4 T cells are also expressed as a percentage of CD3 T cells, since CD4-positive cells are a subset of CD3-positive T cells. CD4 T cell recovery experiments illustrate that n-nonanoyl-RANTES (2-68) can block HIV-1 infection by a macrophage-tropic virus, 242 (now referred to as an R5 virus).

When virus RNA levels were undetectable, they are assigned the lowest value that could have been detected with the available volume of mouse plasma, e.g., 400 copies/ml. the number 400 in this context means 400 copies or fewer, or undetectable by the Roche Amplicor assay. Recovery of human cells at the end of the experiment has to be put into the context of what one would expect in the absence of HIV-1 infection. Historically, CD4 T cell counts account for 30–50% of human CD3 T cells in the peritoneal cavity and 40–70% of total T cells in lymph nodes. All mice in Group 2 (n-nonanoyl-RANTES (2-68) treated) had recovery of CD4-positive T cells in the range expected for uninfected hu-PBL-SCID mice. CD4 T cells accounted for 32–86% of total T cells in peritoneal cavity in the 3 Group 2 mice, and from 52–68% of T cells in LN. By contrast, CD4 T cells in control groups 1 and 3 accounted for 8–12% of total T cells in peritoneal cavity, showing the CD4 T cell depletion previously documented in HIV-1 infected mice. Only one mouse (#124 in group 3) shows lower than expected levels of human cell and HIV-1 viral RNA.

HIV-1 Virus Pools

Figure 8:
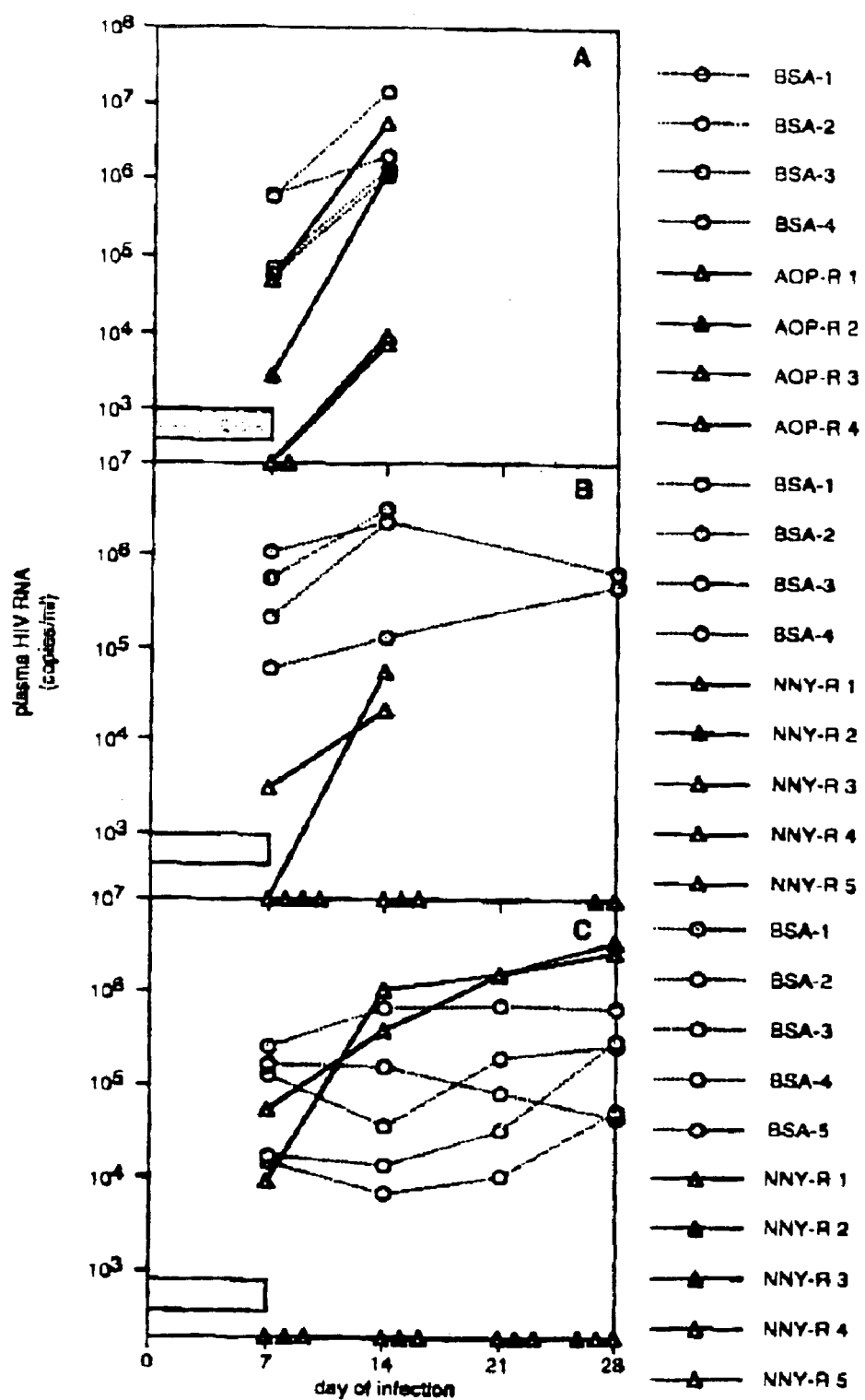
FIG. 8 shows inhibition of HIV-1 infection by AOP- or NNY-RANTES in hu-PBL-SCID mice. CCR5 antagonists were delivered by subcutaneously implanted osmotic pumps at the rate of 2.5 μg/hr beginning 1 day before HIV-1 infection. A single dose of 1 mg of AOP-RANTES (FIG. 8A) or NNY-RANTES (FIGS. 8B and 8C) was administered just prior to HIV-1 challenge. Data presented are plasma HIV RNA copies/ml at 1–4 weeks after infection, and each point represents the value for a single animal. The horizontal bar in each panel represents the duration of continuous AOP- or NNY-RANTES administration.

Infectious stocks of the 242 molecular clone were made by transfecting HEK 293 cells with a fill length molecular clone provided by Dr. Bruce Chesebro. Virus recovered from the culture after 48 hours was used to infect PBMC cultured for 4 days with PHA (2 µg/ml) and for 2 days with IL-2 (20 units/ml). Infectious virus was recovered after 7–10 days of culture, and TCID of the virus determined by end-point titration. Mice were infected with 1000 TCID of virus. Sequencing results showed that the original 242 infectious stock (SEQ ID NO:9) differed from the published sequence (SEQ ID NO:8) by having an H rather than R in position 21 of the V3 loop. This is shown in Table 1. This 242H variant (SEQ ID NO:9) was used for all the experiments depicted in FIG. 8. A second lot of 242 was prepared subsequently and shown to retain the original sequence. The original sequence was also recovered from one animal (NNY-R3 in FIG. 8B), which could have resulted from either mutation or selection of the original R sequence from a virus pool dominated by the 242H variant.

Table 1 shows the V3 envelope sequences of HIV-1 242 recovered from hu-PBL-SCID mice treated with AOP- or NNY-RANTES (SEQ ID NO:2). Sequence in B (SEQ ID NO:8, SEQ ID NO:9 and SEQ ID NO:12) were derived from the two mice in FIG. 8B. The RSX4 241 isolate has an E to Q change at position 24 (Chesebro, et al., supra) and retains the R at position 21 (SEQ ID NO:10). 242H would thus require 2 amino acid changes to change cell tropism and 242R only one amino acid change.

TABLE 1

A.

```
1         5         10        15        20        25        30        34
C T R P N N N T R R S I S I G P G R A F H T T E I I G D I R Q A H C     stock
- - - - - - - - - - - - - - - - - - - - - - - - - - - - - - - - - -     all
```

B.

```
C T R P N N N T R R S I S I G P G R A F R T T E I I G D I R Q A H C
- - - - - - - - - - - - - - - - - - - - R - - - - - - - - - - - -       NNY R3-1
- - - - - - - - - - - - - - - - - - - - R - - - - - - - - - - - -       NNY R3-2
- - - - - - - - - - - - - - - - - - - - R - - - - - - - - - - - -       NNY R3-3
- - - - - - - - - - - - - - - - - - - - R - - - - - - - - - - - -       NNY R3-4
- - - - - - - - - - - - - - - - - - - - R - - - - - - - - - - - -       NNY R3-5
C T R P N N N T R R S I S I G P G R A F H T T E I I G D I R Q A H C
- - - - - - - - - - - - - - - - - - - - - - - - - - - - - - - - -       NNY R5-9
- - - - - - - - - - - - - - - - - - - - - - - - - - - - - - - - -       NNY R5-8
- - - - - - - - - - - - - - - - - - - - - - - - - - - - - - - - -       NNY R5-4
- - - - - - - - - - - - - - - - - - - - - - - - - - - - - - - - -       NNY R5-2
- - - - - - - - - - - - - - - - - - - - - - - - - - - T - - - - -       NNY R5-10
```

Example 19

NNY-RANTES Blocks R5 Virus Entry In Vitro and in hu-PBL-SCID Mice

Methods

Generation of hu-PBL-SCID Mice

SCID mice were bred under specific pathogen flee conditions at Scripps Institute and tested for mouse IgM production at 8 weeks of age. Mice with <5 µg/ml of IgM were engrafted with PBMCs prepared from EBV-seronegative donors from the Scripps General Clinical Research Center pool. SCID mice were injected with 20×106 PBMC intraperitoneally, and checked for plasma levels of human IgG after 12–13 days. Mice with >100 µg/ml of human IgG were used for HIV-1 infection. Each experiment used mice generated from a single, different EBV-negative donor.

In Vitro Assays

PBMC were collected from normal blood by density centrifugation. CD4+ T cells were separated by depletion of other cell types by antibody treatment and immunomagnetic bead separation. Whole PBMC or separated CD4+ T cells were cultured at 5×104 cells per well in 96 well microtiter plates. Cells were activated with PHA and IL2 for 34 days, the medium replaced with concentrations of AOP- or NNY-RANTES (SEQ ID NO:2) ranging from 10 ng/ml to 1 pg/ml, cells incubated for 30 minutes at 37° C., and then infected with 100 TCID of HIV-1 in the continued presence of modified RANTES. After overnight incubation, free virus w as removed and fresh medium containing the original concentration of modified RANTES added. Culture medium was sampled on days 4, 7, and 10 after infection, and p24 HIV capsid antigen measured by ELISA.

Administration of CCR5 Antagonists to Mice

AOP- or NNY-RANTES (SEQ ID NO:2) were dissolved in 0.9% saline at 2.5 mg/ml. Alzet 2001 mini-osmotic pumps were loaded with 200–225 µl of compounds or BSA as a control. Pumps were surgically implanted subcutaneously under halothane anesthesia between the scapulae, and the incision closed with a single wound clip. Pumps were observed for proper placement during the course of the experiment. A single intraperitoneal injection of 1 mg (0.4 ml) of either RANTES compounds or BSA was administered just prior to virus infection.

Virus Infection in Mice

Infection of hu-PBL-SCID mice with HIV-1 was determined by plasma HIV-1 RNA levels measured by the quantitative Roche PCR assay (Amplicor HIV Monitor, Roche Molecular Systems, Somerville, N.J.). The limit of detection was 200–400 copies/ml depending on the plasma volume available. Depletion of CD4$^+$ T cells was measured by flow cytometry. Cells recovered from the peritoneal cavity or regional lymph nodes of hu-PBL-SCID mice were stained with fluorescein- or phycoerythrin-labeled antibodies to human CD3, CD4, CD8, or CD45 and mouse H-2Kd (Phanningen, San Diego, Calif.) and analyzed on a FACScan (Becton Dickinson, Mountain View, Calif.) flow cytometer. CD4$^+$ T cells are expressed as a percentage of total CD3$^+$ cells.

RANTES Levels in Mice

Plasma from hu-PBL-SCID mice was analyzed for RANTES by ELISA (R & D Systems, Minneapolis, Minn.), using standard curves for either AOP- or NNY-RANTES. Plasma was diluted either 1:10 or 1:100 to bring the RANTES (SEQ ID NO:2) concentration into the optimal sensitivity range of the assay.

V3 Envelope Sequences

RNA was extracted from mouse plasma using the Qiagen viral RNA kit (Qiagen, Valencia, Calif.). RNA was convened to cDNA by reverse transcriptase-PCR (RT-PCR). cDNA was amplified by nested PCR using the following primers: outer V3 sense, CCAATTCCCATAGATTATTG (SEQ ID NO:13); outer V3 anti-sense, ATTACAGTAGAAAAATTC-CCC (SEQ ID NO:14); inner V3 sense, CAGTACAATG-TACACATGGAAFT (SEQ ID NO:15); inner V3 anti-sense, AATTTCTGGGTCCCCTCCTGA (SEQ ID NO:16). The final 356 bp product was cloned using the TOPO TA Cloning Kit (Invitrogen, Carlsbad, Calif.), and the resulting product subject to automated sequencing (ABI, Perkins-Elmer, Foster City, Calif.). The final sequence encodes 54 amino acids 5' of V3 and 50 amino acids 3' of V3. Although only the translated V3 sequence is shown in Table 1, the entire sequence was examined and there were no mutations outside of V3.

Results

Inhibitory Activity of AOP- and NNY-RANTES In Vitro

Figure 7:
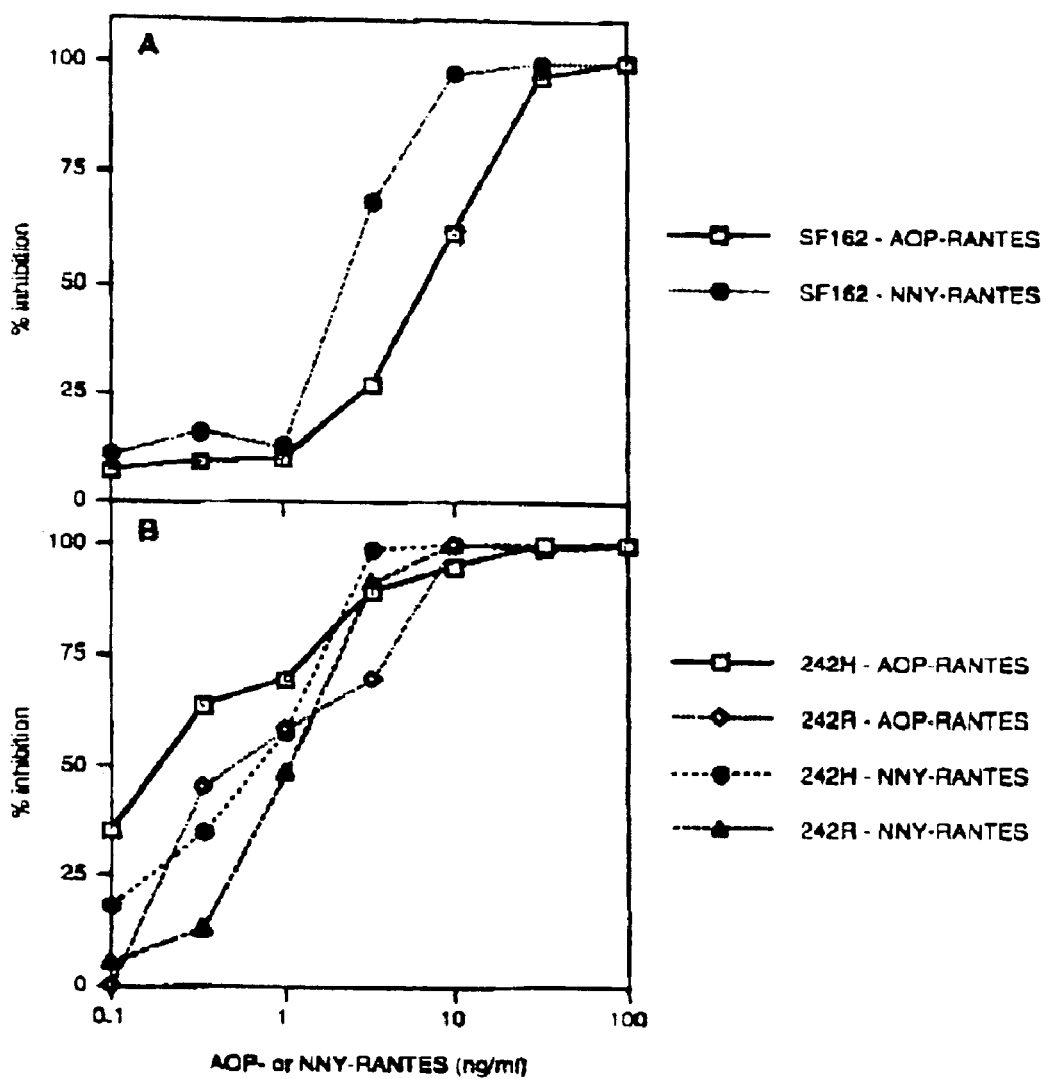
FIG. 7 shows the inhibition of HIV-1 infection by AOP- and NNY-RANTES in cultured primary human PBMC. Virus replication was measured by p24 capsid antigen production after 5–7 days of infection.

The ability of AOP-RANTES and NNY-RANTES to inhibit R5 virus infection, including the R5 242 isolate of Chesebro, et al by in vitro experiments (FIG. 7). The results show that NNY-RANTES (SEQ ID NO:2) and AOP-RANTES were both effective at inhibiting infection of activated PBMC with the SF162 as well as the two variants of the 242 HIV-1 isolate (see Table 1) and failed to inhibit infection with X4 isolates (data not shown). The CCR5 antagonists were able to reduce infection with the R5X4 241 virus (Chesebro, et al., supra) only at higher concentrations, and showed some enhancement of infection at lower concentrations (data not shown). NNY-RANTES was about three-fold more potent than AOP-RANTES at preventing infection with SF162, but was not more potent than AOP-RANTES at inhibiting either the 242H or 242R variants. HIV-1 242R (with a R rather than an H at position 21 of V3) was more resistant to inhibition than 242H with both CCR5 antagonists.

Activity of AOP- and NNY-RANTES in hu-PBL-SCID Mice

Three replicate experiments in hu-PBL-SCID mice were conducted to evaluate the in vivo efficacy of AOP- or NNY-RANTES (SEQ ID NO:2). Because of their rapid clearance from plasma, the CCR5 antagonists were administered at the rate of 2.5 µg/hr by continuous infusion using subcutaneously implanted osmotic pumps. In addition, a single dose of 1 mg (~50 mg/kg) of each antagonist was injected just prior to virus infection. Serial plasma HIV RNA determinations were performed on the treated and control hu-PBL-SCID mice following infection with HIV-1 242. In the experiment shown in FIG. 8A, mice were infused with AOP-RANTES or BSA as a control. Two of the four mice treated with AOP-RANTES had undetectable viral RNA levels at the end of the 7 day infusion period, but virus levels increased in all mice once AOP-RANTES administration was halted. The one animal with viral RNA levels in the control range during treatment (AOP-R 4 in FIG. 8A) also had lower plasma levels of AOP-RANTES (See Table 2). AOP-RANTES was capable of reducing viral load but could not prevent HIV-1 infection despite plasma levels that were fully inhibitory in vitro (see FIG. 7). The inhibitory capacity of NNY-RANTES was tested in the next two experiments using BSA as a control. The results of the first experiment are shown in FIG. 8B. Four of 5 hu-PBL-SCID infused with NNY-RANTES had undetectable viral RNA levels at the end of the infusion period, and only 1 animal subsequently developed viremia (NNY-R 3 in FIG. 8B). NNY-RANTES treatment was thus successful in preventing R5 HIV-1 infection in 3 of 5 mice despite achieving lower plasma concentrations (Table 1) than AOP-RANTES. This experiment was repeated using a different human donor to generate hu-PBL-SCID mice. The results (FIG. 8C) were similar, with NNY-RANTES again preventing infection in 3 of 5 mice.

Table 2 sets forth data as to the recovery of CD4$^+$ human T cells, antagonist levels, and plasma HIV RNA in hu-PBL-SCID mice treated with CCR5 antagonists. Steady-state plasma levels of N-modified RANTES in hu-PBL-SCID mice are shown to be 3.63±0.8 ng/ml for AOP-RANTES and 0.76±0.04 and 0.59±0.16 ng/ml for NNY-RANTES.

TABLE 2

| Exp. | Mouse | day 7 N-RANTES ng/ml | day 14 % CD4+ T cells | day 14 HIV RNA $\log_{10}$ copies/ml |
|---|---|---|---|---|
| A | AOP-R 1 | 4.51 | 17.1 | 3.98 |
|   | AOP-R 2 | 4.77 | 29.2 | 6.07 |
|   | AOP-R 3 | 4.03 | 27.7 | 3.86 |
|   | AOP-R 4 | 1.24 | 14.3 | 6.72 |
|   | mean ± SE | 3.63 ± 0.8 | 22.1 ± 3.7 | 5.16 + 0.73 |
|   | BSA 1 | <0.01 | 3.5 | 7.16 |
|   | BSA 2 | <0.01 | 11.9 | 6.06 |
|   | BSA 3 | <0.01 | 6.2 | 6.31 |
|   | BSA 4 | <0.01 | 4.4 | 6.12 |
|   | mean ± SE | — | 6.5 ± 1.9 | 6.41 ± 0.25 |
| B | NNY-R 1 | 0.82 | 86.1 | <2.30[a] |
|   | NNY-R 2 | 0.68 | — | <2.30 |
|   | NNY-R 3 | 0.86 | 32.7 | 4.72 |
|   | NNY-R 4 | 0.70 | — | <2.30 |
|   | NNY-R 5 | 0.71 | 47.9 | 4.32 |
|   | mean ± SE | 0.76 ± 0.04 | 55.6 ± 15.9 | — |
|   | BSA 1 | <0.01 | 11.7 | 6.49 |
|   | BSA 2 | <0.01 | 12.3 | 6.36 |
|   | BSA 3 | <0.01 | — | 5.12 |
|   | BSA 4 | <0.01 | — | 6.34 |
|   | mean ± SE | — | 12.0 ± 0.3 | 6.08 ± 0.32 |
| C | NNY-R 1 | 0.49 | nd[b] | <2.30 |
|   | NNY-R 2 | 0.41 | nd | <2.30 |
|   | NNY-R 3 | 1.23 | nd | <2.30 |
|   | NNY-R 4 | 0.38 | nd | 6.02 |
|   | NNY-R 5 | 0.43 | nd | 5.59 |
|   | mean ± SE | 0.59 ± 0.16 | — | — |
|   | BSA 1 | <0.01 | nd | 6.49 |
|   | BSA 2 | <0.01 | nd | 6.36 |
|   | BSA 3 | <0.01 | nd | 5.12 |
|   | BSA 4 | <0.01 | nd | 4.56 |
|   | BSA 5 | <0.01 | nd | 5.21 |
|   | mean ± SE | — | — | 4.72 ± 0.36 |

[a]indicates that the data was below the limit of detection of 200 copies/ml
[b]not done The relative survival of human CD4+ T lymphocytes in hu-PBL-SCID mice treated with CCR5 antagonists was also measured. Both AOP- and NNY-RANTES were able to slow the depletion of CD4+ T cells, even in mice where HIV-1 infection was not prevented (See Table 2).

AOP- and NNY-RANTES Do Not Select for Co-Receptor Switch Variants

To determine if virus from hu-PBL-SCID mice that became infected despite treatment with AOP-or NNY-RANTES (SEQ ID NO:2) was evading the antagonists by mutating from CCR5 to CXCR4 co-receptor utilization, proviral DNA envelope genes were amplified and the region surrounding the V3 loop was sequenced, a critical determinant of co-receptor usage (Cocchi, et al., *Nature Med.* 2:1244–1247 (1996)). V3 sequences observed in the mice are shown in Table 1. In the first experiment (FIG. 8A), all mice treated with AOP-RANTES had the same sequence as the starting 242 virus isolate (which was found to contain an H in place of the published R at position 21, a change that had occurred prior to the initiation of these experiments). In the second experiment (FIG. 8B), HV-1 recovered from the two mice that became infected despite treatment with NNY-RANTES differed in the V3 sequence. One mouse had the sequence of the starting 242 isolate (except for one clone with a replacement mutation at position 29), while the other mouse showed a reversion of the H at position 21 to the R present in the original molecular clone. The presence of H or R at position 21 in these isolates did not impact CCR5 usage but did impact susceptibility to NNY-RANTES (FIG. 7B). These results show that although sequence variation was occurring and there may have been selection for sequence variants that were less sensitive to NNY-RANTES inhibition, there was not rapid selection for HIV-1 variants that used alternative co-receptors for viral entry.

Example 19 establishes that NNY-RANTES is more effective than AOP-RANTES in preventing HIV-1 infection, and that neither antagonist selected for viruses capable of utilizing other co-receptors for virus entry. These results show that it is possible to block HIV-1 infection with N-terminally modified RANTES compounds in vivo. Inhibition of virus infection occurred with plasma levels of 0.4–0.9 ng/ml of NNY-RANTES and 4–5 ng/ml of AOP-RANTES during continuous administration of the antagonists, levels that are lower than the average concentration (~20 ng/ml) of native RANTES in human plasma (Weiss, et al., *J. Infect. Dis.* 176:1621–1624 (1997)). There has been one previous report of a chemokine receptor antagonist (AMD3100) that displayed efficacy against X4 HIV-1 infection in mice, albeit at higher concentrations (Datema, et al., *Antimicrob. Agents Chemother.* 40:750–754 (1996)), but this is the first report of antiviral activity of a CCR5 antagonist in vivo.

NNY-RANTES is as effective as a potent neutralizing antibody at preventing HIV-1 infection of hu-PBL-SCID mice (Parren, et al., *AIDS* 9:1–6 (1995) and Gauduin, et al., *Nat Med.* 3:1389–1393 (1997)). Mice that were not protected from infection had lower vital RNA levels and higher CD4+ T cell counts than controls, suggesting that CCR5 antagonists may be useful in treating established infection.

These results also suggest that native RANTES concentrations in plasma are generally too low to be a common explanation for virus resistance in exposed, uninfected individuals (Paxton, et al., *Virology* 244:66–73 (1998)). The in vitro inhibitory concentrations of natural CCR5 ligands are found to be in the 10–100 ng/ml range (Paxton, et al., supra and Trkola, et al., *J. Virol.* 72:396–404 (1998)), which is 10–100 fold higher than inhibitory concentrations for AOP- and NNY-RANTES in vitro (Simmons, et al., supra) and in vivo (data in this Example). The normal plasma RANTES levels in most normal individuals are likely to be too low to block virus infection, although some exposed, uninfected individuals have CD4+ T cells with high enough RANTES secretion to potentially provide local protection (Paxton, et al., supra).

The absence of co-receptor switch variants following either AOP- or NNY-RANTES administration is consistent with the slow rate of development of X4 viruses in infected humans The absence of co-receptor switch variants following either AOP- or NNY-RANTES administration is consistent with the slow rate of development of X4 viruses in infected humans (Schuitemaker, et al., *J. Virol.* 65:356–363 (1991); Tersmette, et al., *Lancet* 1:983–985 (1989); and Connor, et al., *J. Virol.* 67:1772–1777 (1993)). Few mutations are required to change co-receptor usage (Speck, et al., *J. Virol.* 71:7136–7139 (1997)), suggesting that there must be significant biological barriers to switching from the R5 to the X4 virus phenotype. In addition, therapies that target cellular rather than viral proteins are less likely to select for escape mutations. Therapies with multiple chemokine receptor antagonists may also reduce the chance for escape mutations. It appears that one virus (242R, FIG. 7) with reduced sensitivity to NNY-RANTES emerged during treatment, so mutations that alter sensitivity to CCR5 antagonists without changing co-receptor usage may be anticipated. Nonetheless, these would be less troubling than selection for more pathogenic X4 variants. The present in vivo results thus support the continuing development of co-receptor antagonists as viable candidates for the therapy of HIV-1 infection (Cairns, et al., *Nature Med.* 4:563–568 (1998)).

Example 20

Capsule Formulation

This example illustrates the preparation of a representative pharmaceutical formulation for oral administration.

| Ingredients | Quantity per capsule (mg) |
| --- | --- |
| Active ingredient | 200 |
| lactose, spray-dried | 148 |
| magnesium stearate | 2 |

The above ingredients are mixed and introduced into a hard-shell gelatin capsule.

Example 21

Tablet Formulation

This example illustrates the preparation of another representative pharmaceutical formulation for oral administration. A tablet for oral administration is prepared having the following composition:

| Ingredients | Quantity (mg/tablet) |
| --- | --- |
| Active ingredient | 400 |
| corn starch | 50 |
| lactose | 145 |
| magnesium stearate | 5 |

The above ingredients are mixed intimately and pressed into single scored tablets.

Example 22

Oral Formulation

This example illustrates the preparation of a representative suspension for oral administration.

| Ingredients | Quantity |
| --- | --- |
| Active ingredient | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Example 23

Injectable Formulation

An injectable preparation buffered to a suitable pH is prepared having the following composition:

| Ingredients | Quantity |
| --- | --- |
| Active ingredient | 0.2 g |
| Sodium Acetate Buffer Soln (0.4 M) | 2.0 ml |
| HCl (1N) or NaOH (1N) | q.s. to suitable pH |
| water (distilled, sterile) | q.s. to 20 ml |

Example 24

Topical Formulation

This example illustrates the preparation of a representative pharmaceutical formulation for topical application.

| Ingredients | Quantity (g) |
| --- | --- |
| Active ingredient | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60–70° C. with stirring. A sufficient quantity of water at 60° C. is then added with vigorous stirring to emulsify the ingredients, and water then added q.s. to 100 g.

Example 25

Suppository Formulation

A suppository totaling 2.5 grams is prepared having the following composition:

| Ingredients | Quantity |
| --- | --- |
| Active ingredient | 500 mg |
| witepsol H-15* | q.s. to 2.5 g |

*triglycerides of saturated vegetable fatty acid; a product of HULS, Inc., New Jersey.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A compound of the formula:

$R^1$-RANTES (2-68)

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond;
and n is an integer of 4–8;
and in which RANTES (2-68) is a polypeptide having the sequence: PYSSDT TPCCFAYIAR PLPRAHIKEY FYTSGKCSNP AVVFVTRKNR QVCANPEKKW VREYINSLEM S (SEQ ID No. 2) or is a polypeptide having a variant of said sequence, the variant sequence having at least 80% sequence homology with said sequence;
wherein said compound inhibits HIV-1 R5 virus infection of PBMCs in vitro;
or a pharmaceutically acceptable salt thereof.

2. The compound of claim 1, wherein n is 4 and X is —C(O)—NH—$CH_2$—C(O)—.

3. The compound of claim 1, wherein n is 5 and X is —NH—$CH_2$—C(O)—.

4. The compound of claim 1, wherein n is 7 and X is —C(O)—.

5. The compound of claim 1, wherein n is 8 and X is a covalent bond.

6. The compound of claim 1, wherein n is 4 and X is —ONH—$CH_2$—C(O)—.

7. The compound of claim 1, wherein n is 5 and X is —CH=CH—C(O)—.

8. The compound of claim 1, wherein n is 4 and X is —O$CH_2$—$CH_2$—C(O)—.

9. A pharmaceutical composition, which composition comprises a therapeutically effective amount of a compound of the formula:

$R^1$-RANTES (2-68)

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond; and n is an integer of 4–8;
and in which RANTES (2-68) is a polypeptide having the sequence:
PYSSDT TPCCFAYIAR PLPRAHIKEY FYTSGKCSNP AVVFVTRKNR QVCANPEKKW VREYINSLEM S (SEQ ID No. 2) or is a polypeptide having a variant of said sequence, the variant sequence having at least 80% sequence homology with said sequence;
wherein said compound inhibits HIV-1 R5 virus infection of PBMCs in vitro;
or a pharmaceutically acceptable salt thereof;
in admixture with one or more pharmaceutically acceptable excipients.

10. The pharmaceutical composition of claim 9, wherein N is 4 and X is —C(O)—NH—$CH_2$—C(O)—.

11. The pharmaceutical composition of claim 9, wherein N is 5 and X is —NH$CH_2$—C(O)—.

12. The pharmaceutical composition of claim 9, wherein N is 7 and X is —C(O)—.

13. The pharmaceutical composition of claim 9, wherein N is 8 and X is a covalent bond.

14. The pharmaceutical composition of claim 9, wherein N is 4 and X is —ONH—$CH_2$—C(O)—.

15. The pharmaceutical composition of claim 9, wherein N is 5 and X is —CH=CH—C(O)—.

16. The pharmaceutical composition of claim 9, wherein N is 4 and X is —O$CH_2$—$CH_2$—C(O)—.

17. A compound of the formula:

$R^1$-RANTES (2-68)

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond;
and n is an integer of 4–8;

and in which RANTES (2-68) is a polypeptide having the sequence: PYSSDT TPCCFAYIAR PLPRAHIKEY FYTSGKCSNP AVVFVTRKNR QVCANPEKKW VREYINSLEM S (SEQ ID No. 2) or is a polypeptide having a variant of said sequence, the variant sequence having at least 80% sequence homology with said sequence;

wherein said compound binds to the RANTES CCR5 receptor;

or a pharmaceutically acceptable salt thereof.

18. A pharmaceutical composition, which composition comprises a therapeutically effective amount of a compound of the formula:

$$R^1\text{-RANTES (2-68)}$$

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond;
and n is an integer of 4–8;

and in which RANTES (2-68) is a polypeptide having the sequence: PYSSDT TPCCFAYIAR PLPRAHIKEY FYTSGKCSNP AVVFVTRKNR QVCANPEKKW VREYINSLEM S (SEQ ID No. 2) or is a polypeptide having a variant of said sequence, the variant sequence having at least 80% sequence homology with said sequence;

wherein said compound binds to the RANTES CCR5 receptor;

or a pharmaceutically acceptable salt thereof;

in admixture with one or more pharmaceutically acceptable excipients.

19. A compound of the formula:

$$R^1\text{-RANTES (2-68)}$$

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond;
and n is an integer of 4–8;

and in which RANTES (2-68) is a polypeptide having the sequence: PYSSDT TPCCFAYIAR PLPRAHIKEY FYTSGKCSNP AVVFVTRKNR QVCANPEKKW VREYINSLEM S (SEQ ID No. 2) or variant of said sequence having from 1 to 20 single amino acid deletions, insertions or substitutions relative to said sequence;

wherein said compound inhibits HIV-1 R5 virus infection of PBMCs in vitro;

or a pharmaceutically acceptable salt thereof.

20. A pharmaceutical composition, which composition comprises a therapeutically effective amount of a compound of the formula:

$$R^1\text{-RANTES (2-68)}$$

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond;
and n is an integer of 4–8;

and in which RANTES (2-68) is a polypeptide having the sequence: PYSSDT TPCCFAYIAR PLPRAHIKEY FYTSGKCSNP AVVFVTRKNR QVCANPEKKW VREYINSLEM S (SEQ ID No. 2) or variant of said sequence having from 1 to 20 single amino acid deletions, insertions or substitutions relative to said sequence;

wherein said compound inhibits HIV-1 R5 virus infection of PBMCs in vitro;

or a pharmaceutically acceptable salt thereof;

in admixture with one or more pharmaceutically acceptable excipients.

21. A compound of the formula:

$$R^1\text{-RANTES (2-68)}$$

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond;
and n is an integer of 4–8;

and in which RANTES (2-68) is a polypeptide having the sequence: PYSSDT TPCCFAYIAR PLPRAHIKEY FYTSGKCSNP AVVFVTRKNR QVCANPEKKW VREYINSLEM S (SEQ ID No. 2) or variant of said sequence having from 1 to 20 single amino acid deletions, insertions or substitutions relative to said sequence;

wherein said compound binds to the RANTES CCR5 receptor;

or a pharmaceutically acceptable salt thereof.

22. A pharmaceutical composition, which composition comprises a therapeutically effective amount of a compound of the formula:

$$R^1\text{-RANTES (2-68)}$$

where $R^1$ is $CH_3$—$(CH_2)_n$—X—; in which
X is —C(O)—NH—$CH_2$—C(O)—, —NH$CH_2$—C(O)—, —ONH—$CH_2$—C(O)—, —O$CH_2$—$CH_2$—C(O)—, —CH=CH—C(O)—, —C(O)—, or a covalent bond;
and n is an integer of 4–8;

and in which RANTES (2-68) is a polypeptide having the sequence: PYSSDT TPCCFAYIAR PLPRAHIKEY FYTSGKCSNP AVVFVTRKNR QVCANPEKKW VREYINSLEM S (SEQ ID No. 2) or variant of said sequence having from 1 to 20 single amino acid deletions, insertions or substitutions relative to said sequence;

wherein said compound binds to the RANTES CCR5 receptor;

or a pharmaceutically acceptable salt thereof;

in admixture with one or more pharmaceutically acceptable excipients.

* * * * *

SEQUENCE LISTING

<160> NUMBER OF SEQ ID NOS: 16

<210> SEQ ID NO 1
<211> LENGTH: 68
<212> TYPE: PRT
<213> ORGANISM: Homo sapiens

<400> SEQUENCE: 1

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
 65

<210> SEQ ID NO 2
<211> LENGTH: 67
<212> TYPE: PRT
<213> ORGANISM: Homo sapiens

<400> SEQUENCE: 2

Pro Tyr Ser Ser Asp Thr Thr Pro Cys Cys Phe Ala Tyr Ile Ala Arg
 1               5                  10                  15

Pro Leu Pro Arg Ala His Ile Lys Glu Tyr Phe Tyr Thr Ser Gly Lys
            20                  25                  30

Cys Ser Asn Pro Ala Val Val Phe Val Thr Arg Lys Asn Arg Gln Val
        35                  40                  45

Cys Ala Asn Pro Glu Lys Lys Trp Val Arg Glu Tyr Ile Asn Ser Leu
    50                  55                  60

Glu Met Ser
 65

<210> SEQ ID NO 3
<211> LENGTH: 32
<212> TYPE: PRT
<213> ORGANISM: Homo sapiens

<400> SEQUENCE: 3

Pro Tyr Ser Ser Asp Thr Thr Pro Cys Cys Phe Ala Tyr Ile Ala Arg
 1               5                  10                  15

Pro Leu Pro Arg Ala His Ile Lys Glu Tyr Phe Tyr Thr Ser Gly Lys
            20                  25                  30

<210> SEQ ID NO 4
<211> LENGTH: 35
<212> TYPE: PRT
<213> ORGANISM: Homo sapiens

<400> SEQUENCE: 4

Cys Ser Asn Pro Ala Val Val Phe Val Thr Arg Lys Asn Arg Gln Val
 1               5                  10                  15

Cys Ala Asn Pro Glu Lys Lys Trp Val Arg Glu Tyr Ile Asn Ser Leu
            20                  25                  30

Glu Met Ser

35

<210> SEQ ID NO 5
<211> LENGTH: 68
<212> TYPE: PRT
<213> ORGANISM: Homo sapiens

<400> SEQUENCE: 5

Gly Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
             20                  25                  30

Lys Cys Ser Asn Pro Ala Val Val Phe Val Thr Arg Lys Asn Arg Gln
         35                  40                  45

Val Cys Ala Asn Pro Glu Lys Lys Trp Val Arg Glu Tyr Ile Asn Ser
     50                  55                  60

Leu Glu Met Ser
 65

<210> SEQ ID NO 6
<211> LENGTH: 33
<212> TYPE: PRT
<213> ORGANISM: Homo sapiens

<400> SEQUENCE: 6

Gly Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
             20                  25                  30

Lys

<210> SEQ ID NO 7
<211> LENGTH: 35
<212> TYPE: PRT
<213> ORGANISM: Homo sapiens

<400> SEQUENCE: 7

Cys Thr Arg Pro Asn Asn Asn Thr Arg Lys Ser Ile His Ile Gly Pro
 1               5                  10                  15

Gly Arg Ala Phe Tyr Thr Thr Gly Glu Ile Ile Gly Asp Ile Arg Gln
             20                  25                  30

Ala His Cys
         35

<210> SEQ ID NO 8
<211> LENGTH: 34
<212> TYPE: PRT
<213> ORGANISM: Homo sapiens

<400> SEQUENCE: 8

Cys Thr Arg Pro Asn Asn Asn Thr Arg Arg Ser Ile Ser Ile Gly Pro
 1               5                  10                  15

Gly Arg Ala Phe Arg Thr Thr Glu Ile Ile Gly Asp Ile Arg Gln Ala
             20                  25                  30

His Cys

<210> SEQ ID NO 9
<211> LENGTH: 34
<212> TYPE: PRT
<213> ORGANISM: Homo sapiens

```
<400> SEQUENCE: 9

Cys Thr Arg Pro Asn Asn Asn Thr Arg Arg Ser Ile Ser Ile Gly Pro
 1               5                  10                  15

Gly Arg Ala Phe His Thr Thr Glu Ile Ile Gly Asp Ile Arg Gln Ala
            20                  25                  30

His Cys

<210> SEQ ID NO 10
<211> LENGTH: 34
<212> TYPE: PRT
<213> ORGANISM: Homo sapiens

<400> SEQUENCE: 10

Cys Thr Arg Pro Asn Asn Asn Thr Arg Arg Ser Ile Ser Ile Gly Pro
 1               5                  10                  15

Gly Arg Ala Phe Arg Thr Thr Gln Ile Ile Gly Asp Ile Arg Gln Ala
            20                  25                  30

His Cys

<210> SEQ ID NO 11
<211> LENGTH: 34
<212> TYPE: PRT
<213> ORGANISM: Homo sapiens

<400> SEQUENCE: 11

Cys Thr Arg Pro Asn Asn Asn Thr Arg Arg Ser Ile Ser Ile Gly Pro
 1               5                  10                  15

Gly Arg Ala Phe Arg Thr Thr Gln Ile Val Gly Asn Leu Arg Gln Ala
            20                  25                  30

His Cys

<210> SEQ ID NO 12
<211> LENGTH: 34
<212> TYPE: PRT
<213> ORGANISM: Homo sapiens

<400> SEQUENCE: 12

Cys Thr Arg Pro Asn Asn Asn Thr Arg Arg Ser Ile Ser Ile Gly Pro
 1               5                  10                  15

Gly Arg Ala Phe His Thr Thr Glu Ile Ile Gly Asp Thr Arg Gln Ala
            20                  25                  30

His Cys

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
ccaattccca tacattattg                                              20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer
```

```
<400> SEQUENCE: 14
attacagtag aaaaattccc c                                         21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 15
cagtacaatg tacacatgga att                                       23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 16
aatttctggg tcccctcctg a                                         21
```